US010058313B2

(12) United States Patent
Manasse

(10) Patent No.: US 10,058,313 B2
(45) Date of Patent: Aug. 28, 2018

(54) TRANSAPICAL VALVE REPLACEMENT

(71) Applicant: Sorin Group Italia S.r.l., Milan (IT)

(72) Inventor: Eric Manasse, Milan (IT)

(73) Assignee: Sorin Group Italia S.r.l., Milan (IT)

(*) Notice: Subject to any disclaimer, the term of this patent is extended or adjusted under 35 U.S.C. 154(b) by 310 days.

(21) Appl. No.: 15/153,475

(22) Filed: May 12, 2016

(65) Prior Publication Data

US 2016/0256143 A1   Sep. 8, 2016

Related U.S. Application Data

(62) Division of application No. 13/478,729, filed on May 23, 2012.

(60) Provisional application No. 61/489,435, filed on May 24, 2011.

(51) Int. Cl.
*A61B 17/34* (2006.01)
*A61B 17/00* (2006.01)
*A61F 2/24* (2006.01)

(52) U.S. Cl.
CPC .... *A61B 17/00234* (2013.01); *A61B 17/3423* (2013.01); *A61F 2/2436* (2013.01); *A61B 17/0057* (2013.01); *A61B 2017/00247* (2013.01); *A61B 2017/00292* (2013.01); *A61B 2017/00575* (2013.01)

(58) Field of Classification Search
CPC ............. A61B 17/34; A61B 17/00234; A61B 17/3417; A61B 17/3421; A61B 17/3423; A61B 2017/3425; A61B 2017/00247; A61B 2017/00243
USPC .......................................... 606/185; 623/2.11
See application file for complete search history.

(56) References Cited

U.S. PATENT DOCUMENTS

| 3,514,131 A | 5/1970 | McKinney |
| 3,671,979 A | 6/1972 | Moulopoulos |
| 4,011,947 A | 3/1977 | Sawyer |
| 4,056,854 A | 11/1977 | Boretos et al. |
| 4,220,151 A | 9/1980 | Whitney |
| 4,477,930 A | 10/1984 | Totten et al. |
| 4,601,706 A | 7/1986 | Aillon |
| 4,624,822 A | 11/1986 | Arru et al. |
| 4,684,364 A | 8/1987 | Sawyer et al. |
| 4,722,725 A | 2/1988 | Sawyer et al. |

(Continued)

FOREIGN PATENT DOCUMENTS

| DE | 19546692 C2 | 6/1997 |
| DE | 29919625 U1 | 2/2000 |

(Continued)

OTHER PUBLICATIONS

European Search Report and Search Opinion of European Patent Application No. 07115960.2, dated Jan. 24, 2008.

(Continued)

*Primary Examiner* — Melanie Tyson
(74) *Attorney, Agent, or Firm* — Faegre Baker Daniels LLP

(57) ABSTRACT

Techniques for reaching the interior of the heart, such as for aortic valve replacement, can combine elements of percutaneous implantation methods and elements of surgical implantation methods. In some instances, aortic valve replacement may include a dual transapical approach in which a transfemoral approach is used to reach the apex of the patient's heart from inside the left ventricle while a minimally invasive surgical procedure provides access to the exterior of the apex via an intercostal approach.

17 Claims, 21 Drawing Sheets

(56) References Cited

U.S. PATENT DOCUMENTS

| | | |
|---|---|---|
| 4,732,152 A | 3/1988 | Wallsten et al. |
| 4,758,151 A | 7/1988 | Arru et al. |
| 4,777,951 A | 10/1988 | Cribier et al. |
| 4,784,644 A | 11/1988 | Sawyer et al. |
| 4,994,077 A | 2/1991 | Dobben |
| 5,057,092 A | 10/1991 | Webster, Jr. |
| 5,084,151 A | 1/1992 | Vallana et al. |
| 5,123,919 A | 6/1992 | Sauter et al. |
| 5,133,845 A | 7/1992 | Vallana et al. |
| 5,181,911 A | 1/1993 | Shturman |
| 5,201,757 A | 4/1993 | Heyn et al. |
| 5,287,848 A | 2/1994 | Cubb |
| 5,304,189 A | 4/1994 | Goldberg et al. |
| 5,312,393 A | 5/1994 | Mastel |
| 5,332,402 A | 7/1994 | Teitelbaum |
| 5,370,684 A | 12/1994 | Vallana et al. |
| 5,370,685 A | 12/1994 | Stevens |
| 5,387,247 A | 2/1995 | Vallana et al. |
| 5,397,351 A | 3/1995 | Pavcnik et al. |
| 5,411,552 A | 5/1995 | Andersen et al. |
| 5,423,886 A | 6/1995 | Arru et al. |
| 5,433,723 A | 7/1995 | Lindenberg et al. |
| 5,445,608 A | 8/1995 | Chen et al. |
| 5,445,646 A | 8/1995 | Euteneuer et al. |
| 5,545,214 A | 8/1996 | Stevens |
| 5,554,185 A | 9/1996 | Block et al. |
| 5,556,414 A | 9/1996 | Turi |
| 5,662,712 A | 9/1997 | Pathak et al. |
| 5,693,083 A | 12/1997 | Baker et al. |
| 5,766,151 A | 6/1998 | Valley et al. |
| 5,772,693 A | 6/1998 | Brownlee |
| 5,782,811 A | 7/1998 | Samson et al. |
| 5,824,064 A | 10/1998 | Taheri |
| 5,840,081 A | 11/1998 | Andersen et al. |
| 5,849,005 A | 12/1998 | Garrison et al. |
| 5,855,597 A | 1/1999 | Jayaraman |
| 5,855,601 A | 1/1999 | Bessler et al. |
| 5,871,489 A | 2/1999 | Ovil |
| 5,925,063 A | 7/1999 | Knosravi |
| 5,951,600 A | 9/1999 | Lemelson |
| 5,954,766 A | 9/1999 | Zadno Azizi et al. |
| 5,957,949 A | 9/1999 | Leonhardt et al. |
| 5,968,068 A | 10/1999 | Dehdashtian et al. |
| 5,980,570 A | 11/1999 | Simpson |
| 6,010,530 A | 1/2000 | Goicoechea |
| 6,010,531 A | 1/2000 | Donlon et al. |
| 6,019,756 A | 2/2000 | Mueller et al. |
| 6,019,790 A | 2/2000 | Holmberg et al. |
| 6,029,671 A | 2/2000 | Stevens et al. |
| 6,030,360 A | 2/2000 | Biggs |
| 6,090,099 A | 7/2000 | Samson et al. |
| 6,106,497 A | 8/2000 | Wang |
| 6,125,852 A | 10/2000 | Stevens et al. |
| 6,139,572 A | 10/2000 | Campbell et al. |
| 6,168,614 B1 | 1/2001 | Andersen et al. |
| 6,174,307 B1 | 1/2001 | Daniel et al. |
| 6,251,093 B1 | 6/2001 | Valley et al. |
| 6,299,638 B1 | 10/2001 | Sauter |
| 6,309,382 B1 | 10/2001 | Garrison et al. |
| 6,346,071 B1 | 2/2002 | Mussivand |
| 6,395,017 B1 | 5/2002 | Dwyer et al. |
| 6,402,780 B2 | 6/2002 | Williamson, IV et al. |
| 6,416,474 B1 | 7/2002 | Penner et al. |
| 6,425,916 B1 | 7/2002 | Garrison et al. |
| 6,454,799 B1 | 9/2002 | Schreck |
| 6,458,153 B1 | 10/2002 | Bailey et al. |
| 6,482,228 B1 | 11/2002 | Norred |
| 6,572,642 B2 | 6/2003 | Rinaldi et al. |
| 6,582,462 B1 | 6/2003 | Andersen et al. |
| 6,607,553 B1 | 8/2003 | Healy et al. |
| 6,641,558 B1 | 11/2003 | Aboul Hosn et al. |
| 6,645,197 B2 | 11/2003 | Garrison et al. |
| 6,645,220 B1 | 11/2003 | Huter et al. |
| 6,652,578 B2 | 11/2003 | Bailey et al. |
| 6,685,739 B2 | 2/2004 | DiMatteo et al. |
| 6,726,648 B2 | 4/2004 | Kaplon et al. |
| 6,726,651 B1 | 4/2004 | Robinson et al. |
| 6,726,712 B1 | 4/2004 | Raeder Devens et al. |
| 6,730,118 B2 | 5/2004 | Spenser et al. |
| 6,733,525 B2 | 5/2004 | Yang et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,830,584 B1 | 12/2004 | Seguin |
| 6,830,585 B1 | 12/2004 | Artof et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,913,618 B2 | 7/2005 | Denardo et al. |
| 6,945,957 B2 | 9/2005 | Freyman |
| 6,964,673 B2 | 11/2005 | Tsugita et al. |
| 6,974,464 B2 | 12/2005 | Quijano et al. |
| 6,981,942 B2 | 1/2006 | Khaw et al. |
| 6,991,646 B2 | 1/2006 | Clerc et al. |
| 7,001,423 B2 | 2/2006 | Euteneuer et al. |
| 7,018,406 B2 | 3/2006 | Seguin et al. |
| 7,018,408 B2 | 3/2006 | Bailey et al. |
| 7,041,132 B2 | 5/2006 | Quijano et al. |
| 7,044,966 B2 | 5/2006 | Svanidze et al. |
| 7,077,801 B2 | 7/2006 | Haverich |
| 7,101,396 B2 | 9/2006 | Artof et al. |
| 7,144,364 B2 | 12/2006 | Barbut et al. |
| 7,156,872 B2 | 1/2007 | Strecker |
| 7,195,641 B2 | 3/2007 | Palmaz et al. |
| 7,201,761 B2 | 4/2007 | Woolfson et al. |
| 7,329,279 B2 | 2/2008 | Haug et al. |
| 7,338,467 B2 | 3/2008 | Lutter |
| 7,338,520 B2 | 3/2008 | Bailey et al. |
| 7,374,571 B2 | 5/2008 | Pease et al. |
| RE40,377 E | 6/2008 | Williamson, IV et al. |
| 7,399,315 B2 | 7/2008 | Iobbi |
| 7,544,206 B2 | 6/2009 | Cohn |
| 7,556,646 B2 | 7/2009 | Yang et al. |
| 7,591,843 B1 | 9/2009 | Escano et al. |
| 7,618,432 B2 | 11/2009 | Pedersen et al. |
| 7,635,386 B1 | 12/2009 | Gammie |
| 7,708,775 B2 | 5/2010 | Rowe et al. |
| 7,896,915 B2 | 3/2011 | Guyenot et al. |
| 7,993,393 B2 | 8/2011 | Rihhini et al. |
| 8,057,539 B2 | 11/2011 | Ghione et al. |
| 8,070,799 B2 | 12/2011 | Righini et al. |
| 8,114,154 B2 | 2/2012 | Righini et al. |
| 8,353,953 B2 | 1/2013 | Giannetti et al. |
| 8,403,982 B2 | 3/2013 | Giannetti et al. |
| 8,470,024 B2 | 6/2013 | Ghione et al. |
| 8,475,521 B2 | 7/2013 | Suri et al. |
| 8,486,137 B2 | 7/2013 | Suri et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0039450 A1 | 11/2001 | Pavcnik et al. |
| 2001/0044591 A1 | 11/2001 | Stevens et al. |
| 2002/0029075 A1 | 3/2002 | Leonhardt |
| 2002/0042651 A1 | 4/2002 | Liddicoat et al. |
| 2002/0045846 A1 | 4/2002 | Kaplon et al. |
| 2002/0045929 A1 | 4/2002 | Diaz |
| 2002/0058995 A1 | 5/2002 | Stevens |
| 2002/0099431 A1 | 7/2002 | Armstrong et al. |
| 2002/0107531 A1 | 8/2002 | Schreck et al. |
| 2002/0117264 A1 | 8/2002 | Rinaldi et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0033000 A1 | 2/2003 | DiCaprio et al. |
| 2003/0036795 A1 | 2/2003 | Andersen et al. |
| 2003/0055495 A1 | 3/2003 | Pease et al. |
| 2003/0109924 A1 | 6/2003 | Cribier |
| 2003/0130729 A1 | 7/2003 | Paniagua et al. |
| 2003/0153974 A1 | 8/2003 | Spenser et al. |
| 2003/0163194 A1 | 8/2003 | Quijano et al. |

(56) References Cited

U.S. PATENT DOCUMENTS

| | | |
|---|---|---|
| 2003/0191521 A1 | 10/2003 | Denardo et al. |
| 2003/0191528 A1 | 10/2003 | Quijano et al. |
| 2004/0034411 A1 | 2/2004 | Quijano et al. |
| 2004/0039371 A1 | 2/2004 | Tockman et al. |
| 2004/0039436 A1 | 2/2004 | Spenser et al. |
| 2004/0039442 A1 | 2/2004 | St. Goar et al. |
| 2004/0049266 A1 | 3/2004 | Anduiza et al. |
| 2004/0055606 A1 | 3/2004 | Hendricksen et al. |
| 2004/0078072 A1 | 4/2004 | Tu et al. |
| 2004/0093060 A1 | 5/2004 | Seguin et al. |
| 2004/0093063 A1 | 5/2004 | Wright et al. |
| 2004/0106976 A1 | 6/2004 | Bailey et al. |
| 2004/0127848 A1 | 7/2004 | Freyman |
| 2004/0147993 A1 | 7/2004 | Westlund et al. |
| 2004/0186563 A1 | 9/2004 | Lobbi |
| 2004/0215333 A1 | 10/2004 | Duran et al. |
| 2004/0236170 A1 | 11/2004 | Kim |
| 2004/0249413 A1 | 12/2004 | Allen et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1 | 4/2005 | Gunderson et al. |
| 2005/0096993 A1 | 5/2005 | Pradhan et al. |
| 2005/0104957 A1 | 5/2005 | Okamoto et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0165480 A1 | 7/2005 | Jordan et al. |
| 2005/0197695 A1 | 9/2005 | Stacchino et al. |
| 2005/0240200 A1 | 10/2005 | Bergheim |
| 2005/0251251 A1 | 11/2005 | Cribier |
| 2005/0267493 A1 | 12/2005 | Schreck et al. |
| 2005/0278010 A1 | 12/2005 | Richardson |
| 2006/0004436 A1 | 1/2006 | Amarant et al. |
| 2006/0004439 A1 | 1/2006 | Spenser et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0030922 A1 | 2/2006 | Dolan |
| 2006/0063199 A1 | 3/2006 | Elgebaly et al. |
| 2006/0064054 A1 | 3/2006 | Sakakine et al. |
| 2006/0074271 A1 | 4/2006 | Cotter |
| 2006/0074484 A1 | 4/2006 | Huber |
| 2006/0085060 A1 | 4/2006 | Campbell |
| 2006/0095025 A1 | 5/2006 | Levine et al. |
| 2006/0100639 A1 | 5/2006 | Levin et al. |
| 2006/0135962 A1 | 6/2006 | Kick et al. |
| 2006/0142838 A1 | 6/2006 | Molaei et al. |
| 2006/0142848 A1 | 6/2006 | Gabbay |
| 2006/0178740 A1 | 8/2006 | Stacchino et al. |
| 2006/0195134 A1 | 8/2006 | Crittenden |
| 2006/0195184 A1 | 8/2006 | Lane et al. |
| 2006/0229659 A1 | 10/2006 | Gifford et al. |
| 2006/0241656 A1 | 10/2006 | Starksen et al. |
| 2006/0271081 A1 | 11/2006 | Realyvasquez |
| 2006/0276775 A1 | 12/2006 | Rosenberg et al. |
| 2007/0005131 A1 | 1/2007 | Taylor |
| 2007/0010850 A1 | 1/2007 | Balgobin et al. |
| 2007/0027534 A1 | 2/2007 | Bergheim et al. |
| 2007/0032850 A1 | 2/2007 | Ruiz et al. |
| 2007/0055357 A1 | 3/2007 | Pokorney et al. |
| 2007/0088431 A1 | 4/2007 | Bourang et al. |
| 2007/0100302 A1 | 5/2007 | Dicarlo et al. |
| 2007/0100356 A1 | 5/2007 | Lucatero et al. |
| 2007/0100440 A1 | 5/2007 | Figulla et al. |
| 2007/0112355 A1 | 5/2007 | Salahieh et al. |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0156225 A1 | 7/2007 | George et al. |
| 2007/0162100 A1 | 7/2007 | Gabbay |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0173861 A1 | 7/2007 | Strommer et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0219630 A1 | 9/2007 | Chu |
| 2007/0250097 A1 | 10/2007 | Weitzner et al. |
| 2007/0265702 A1 | 11/2007 | Lattouf |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0097595 A1 | 4/2008 | Gabbay |
| 2008/0140189 A1 | 6/2008 | Nguyen et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0183097 A1 | 7/2008 | Leyde et al. |
| 2008/0208216 A1 | 8/2008 | Cerier |
| 2008/0262507 A1 | 10/2008 | Righini et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0105794 A1 | 4/2009 | Ziarno et al. |
| 2009/0118580 A1 | 5/2009 | Sun et al. |
| 2009/0157174 A1 | 6/2009 | Yoganathan et al. |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171456 A1 | 7/2009 | Kveen et al. |
| 2009/0177275 A1 | 7/2009 | Case |
| 2009/0228093 A1 | 9/2009 | Taylor et al. |
| 2009/0234443 A1 | 9/2009 | Ottma et al. |
| 2009/0240326 A1 | 9/2009 | Wilson et al. |
| 2009/0254165 A1 | 10/2009 | Tabor et al. |
| 2009/0281609 A1 | 11/2009 | Benichou et al. |
| 2009/0281619 A1 | 11/2009 | Le et al. |
| 2010/0191326 A1 | 7/2010 | Alkhatib |
| 2010/0292782 A1 | 11/2010 | Giannetti et al. |
| 2010/0292783 A1 | 11/2010 | Giannetti et al. |
| 2010/0292784 A1 | 11/2010 | Giannetti et al. |
| 2011/0144690 A1 | 6/2011 | Bishop et al. |
| 2012/0053684 A1 | 3/2012 | Righini et al. |
| 2013/0123915 A1 | 5/2013 | Giannetti et al. |

FOREIGN PATENT DOCUMENTS

| | | |
|---|---|---|
| DE | 19857887 A1 | 5/2005 |
| EP | 0133420 B1 | 2/1988 |
| EP | 0155245 B1 | 5/1990 |
| EP | 0515324 B1 | 11/1992 |
| EP | 0637454 B1 | 2/1995 |
| EP | 0592410 B1 | 10/1995 |
| EP | 0512359 B1 | 12/1996 |

(56) References Cited

FOREIGN PATENT DOCUMENTS

| | | |
|---|---|---|
| EP | 0850607 A1 | 7/1998 |
| EP | 0941716 B1 | 9/1999 |
| EP | 1057460 A1 | 12/2000 |
| EP | 1059271 A1 | 12/2000 |
| EP | 1356763 A2 | 10/2003 |
| EP | 1440671 A2 | 10/2003 |
| EP | 0852481 B1 | 2/2004 |
| EP | 1440671 A2 | 7/2004 |
| EP | 1088529 B1 | 6/2005 |
| EP | 0955895 B1 | 8/2005 |
| EP | 1488735 B1 | 6/2007 |
| EP | 1212989 B1 | 1/2008 |
| EP | 1653884 B1 | 6/2008 |
| EP | 1935377 A1 | 6/2008 |
| EP | 1955643 A1 | 8/2008 |
| EP | 1978895 B1 | 10/2008 |
| EP | 1986579 B1 | 11/2008 |
| EP | 1570809 B1 | 1/2009 |
| EP | 2033581 A1 | 3/2009 |
| EP | 2033597 A1 | 3/2009 |
| FR | 2828091 A1 | 2/2003 |
| WO | WO1995011055 A1 | 4/1995 |
| WO | WO1997024989 A1 | 7/1997 |
| WO | WO1998017202 A1 | 4/1998 |
| WO | WO1998029057 A1 | 7/1998 |
| WO | WO1998053761 A1 | 12/1998 |
| WO | WO1999004728 A1 | 2/1999 |
| WO | WO1999012483 A1 | 3/1999 |
| WO | WO1999056665 A1 | 11/1999 |
| WO | WO2000018303 A1 | 4/2000 |
| WO | WO2000041525 A2 | 7/2000 |
| WO | WO2000041652 A1 | 7/2000 |
| WO | WO2001021244 A1 | 3/2001 |
| WO | WO2001062189 A1 | 8/2001 |
| WO | WO2001064137 A1 | 9/2001 |
| WO | WO2001076510 A2 | 10/2001 |
| WO | WO2002041789 A2 | 8/2002 |
| WO | WO2002076348 A1 | 10/2002 |
| WO | WO2002047575 A2 | 12/2002 |
| WO | WO2003047468 A1 | 6/2003 |
| WO | WO2003003943 A2 | 11/2003 |
| WO | WO2003094797 A1 | 11/2003 |
| WO | WO2004019825 A1 | 3/2004 |
| WO | WO2004028399 A2 | 4/2004 |
| WO | WO2004089253 A1 | 10/2004 |
| WO | WO2005046525 A1 | 5/2005 |
| WO | WO2005065200 A2 | 7/2005 |
| WO | WO2005096993 A1 | 10/2005 |
| WO | WO2005104957 A2 | 11/2005 |
| WO | WO2006009690 A1 | 1/2006 |
| WO | WO2006014233 A2 | 2/2006 |
| WO | WO2006054107 A2 | 5/2006 |
| WO | WO2006063199 A2 | 6/2006 |
| WO | WO2006076890 A1 | 7/2006 |
| WO | WO2006086135 A2 | 8/2006 |
| WO | WO2006089517 A1 | 8/2006 |
| WO | WO2006116538 A2 | 11/2006 |
| WO | WO2006135551 A2 | 12/2006 |
| WO | WO2006138173 A2 | 12/2006 |
| WO | WO2007021708 A1 | 2/2007 |
| WO | WO2007033093 A2 | 3/2007 |
| WO | WO2007059252 A1 | 5/2007 |
| WO | WO2007071436 A2 | 6/2007 |
| WO | WO2007076463 A2 | 7/2007 |
| WO | WO2008031103 A2 | 3/2008 |
| WO | WO2008097589 A1 | 8/2008 |
| WO | WO2008125153 A1 | 10/2008 |
| WO | WO2008138584 A1 | 11/2008 |

OTHER PUBLICATIONS

European Search Report Issued in EP 09160184 dated Oct. 22, 2009.
European Search Report issued in EP 11182402, dated Nov. 16, 2011, 5 pages.
European Search Report issued in EP Application 08163752, dated Dec. 29, 2008.
European Search Report Issued in EP Application No. 07115951, dated Sep. 24, 2009, 8 pages.
European Search Report issued in EP Application No. 08159301, dated Dec. 30, 2008, 6 pages.
European Search Report Issued in EP Application No. 09160183, dated Sep. 29, 2009, 6 pages.
European Search Report Issued in EP Application No. 09160186, dated Oct. 6, 2009, 5 pages.
Extended European Search Report issued in EP Application 06126552, dated Jun. 6, 2007, 7 pages.
Extended European Search Report issued in EP Application 06126556, dated Jul. 6, 2007, 13 pages.
Extended European Search Report issued in EP Application 07115960, dated Jan. 24, 2008, 8 pages.
Extended European Search Report issued in EP Application 09158322, dated Sep. 29, 2009, 5 pages.
Ho, Paul C., "Percutaneous aortic valve replacement: A novel design of the delivery and deployment system", Minimally Invasive Therapy, 2008; 17:3; 190-194.
Huber et al., "Direct-Access Valve Replacement: A Novel Approach for Off-Pump Valve Implantation Using Valved Stents", Journal for the American College of Cardiology, pp. 366-370, vol. 46, No. 2, Jul. 19, 2005, ISSN: 0735-1097/05 published on-line Jul. 5, 2005.
Partial European Search Report issued in EP App No. 06126556, dated Apr. 16, 2007, 6 pages.
Partial European Search Report issued in EP Application No. 10155332, dated Jun. 9, 2011, 7 pages.
U.S. Appl. No. 11/612,968, filed Dec. 19, 2006.
U.S. Appl. No. 11/612,974, filed Dec. 19, 2006.
U.S. Appl. No. 11/351,528, filed Sep. 7, 2007.

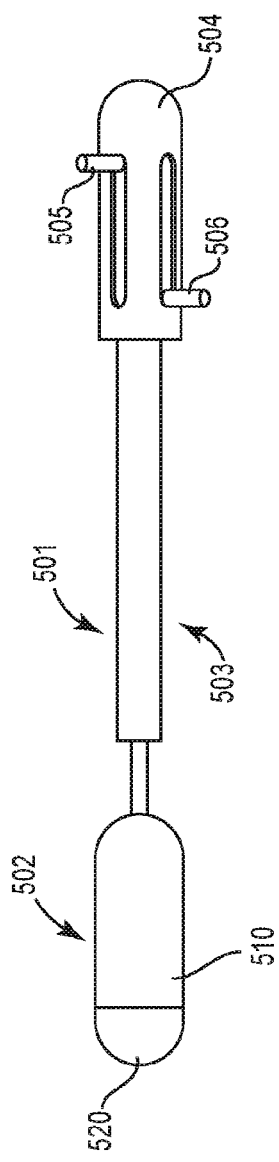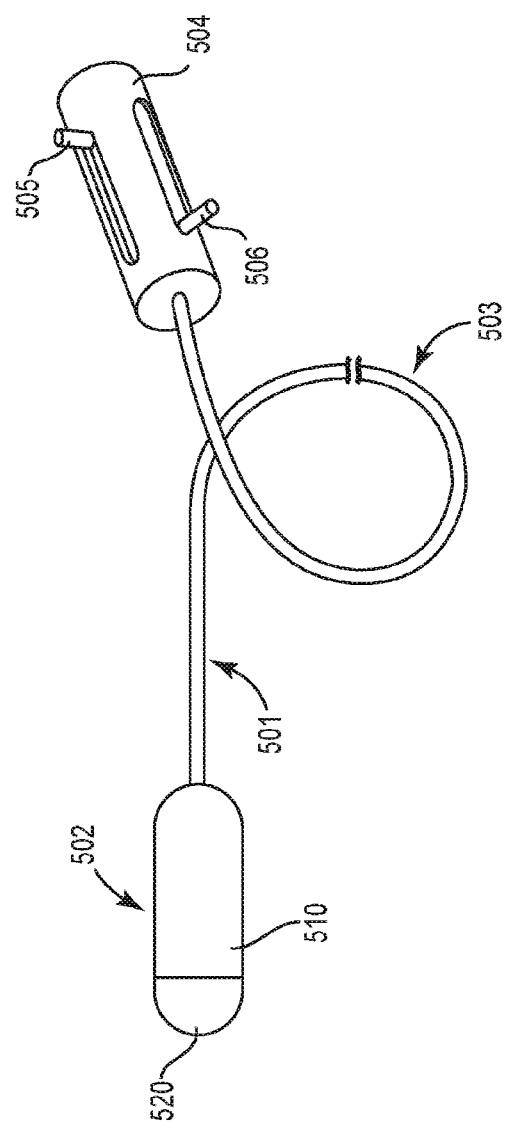
Fig. 21A
Fig. 21B

TRANSAPICAL VALVE REPLACEMENT

CROSS-REFERENCE TO RELATED APPLICATION

This application is a division of application from U.S. application Ser. No. 13/478,729, filed May 23, 2012, which claims the benefit under 35 U.S.C. § 119(e) of U.S. Provisional Application No. 61/489,435, filed May 24, 2011, which is incorporated herein by reference in its entirety.

TECHNICAL FIELD

The disclosure relates generally to any procedure performed within the heart (or its main arteries), including closure of ventricular septal defects, repair of aortic aneurysm, ablation of atrial/ventricular arrhythmia, and valve replacement procedures. More particularly, it relates to transapical valve replacement procedures.

BACKGROUND

Natural heart valves, such as aortic valves, mitral valves, pulmonary valves, and tricuspid valves, often become damaged by disease in such a manner that they fail to maintain bodily fluid flow in a single direction. A malfunctioning heart valve may be stenotic (i.e., calcification of the valve leaflets) or regurgitant (i.e., heart leaflets are wide open). Maintenance of blood flow in a single direction through the heart valve is important for proper flow, pressure, and perfusion of blood through the body. Hence, a heart valve that does not function properly may noticeably impair the function of the heart. Left untreated, valve disease can lead to death. There has been increasing consideration given to the possibility of using, as an alternative to traditional cardiac-valve prostheses, valves designed to be implanted using minimally-invasive surgical techniques or endovascular delivery (so-called "percutaneous valves").

SUMMARY

Example 1 is a transapical method of gaining access to an interior of a patient's heart. A first guidewire may be advanced through the ascending aorta and through the aortic valve to a location within the left ventricle. A guide catheter may be advanced over the first guidewire to the location within the left ventricle. A cutting catheter may be advanced over the first guidewire and a balloon catheter having an inflatable balloon may be advanced over the first guide catheter. The inflatable balloon may be inflated proximate the wall of the left ventricle, and the left ventricle wall may be penetrated using the cutting catheter. The interior of a patient's chest may be accessed through an intercostal space that is disposed above the apex of the patient's heart. An S-shaped catheter may be advanced through the intercostal space such that the S-shaped catheter has a distal end positioned proximate the patient's pericardial sac. The pericardial sac may be penetrated using an instrument advanced through the S-shaped catheter. A distal end of the balloon catheter may be connected to the distal end of the S-shaped catheter and the S-shaped catheter may be withdrawn to lift the apex of the heart.

In Example 2, the method of Example 1 in which the first guidewire is advanced through the patient's vasculature from a femoral access point.

In Example 3, the method of Example 1 or Example 2 in which accessing the interior of a patient's chest includes penetrating the chest wall through an intercostal space using a hollow needle.

In Example 4, the method of any of Examples 1-3 in which the instrument used to penetrate the pericardial sac is a hollow needle.

In Example 5, the method of any of Examples 1-4, further including advancing a port over the balloon catheter.

In Example 6, the method of Example 5, further including delivering a prosthetic valve through the port.

Example 7 is a transapical method of gaining access to an interior of a patient's heart. A first hollow needle may be advanced into a patient's chest through an intercostal space, the intercostal space being above the apex of the patient's heart. An S-shaped catheter may be advanced through the first hollow needle such that the S-shaped catheter has a distal end positioned proximate the patient's pericardial sac. A guidewire may be advanced through the S-shaped catheter. A second hollow needle may be advanced over the guidewire to a position proximate the pericardial sac, and the pericardial sac may be penetrated with the second hollow needle. A catheter bearing a cutting blade may be advanced through the second hollow needle and penetrating the heart wall. A catheter including an inflatable balloon on a distal region of the catheter may be advanced, the inflatable balloon may be inflated, and then the catheter may be partially withdrawn to lift the apex of the heart to a higher position proximate the intercostal space through which the first hollow needle was advanced.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE FIGURES

FIGS. 21A and 21B are schematic illustrations of an embodiment of a delivery device.

Figure 1:
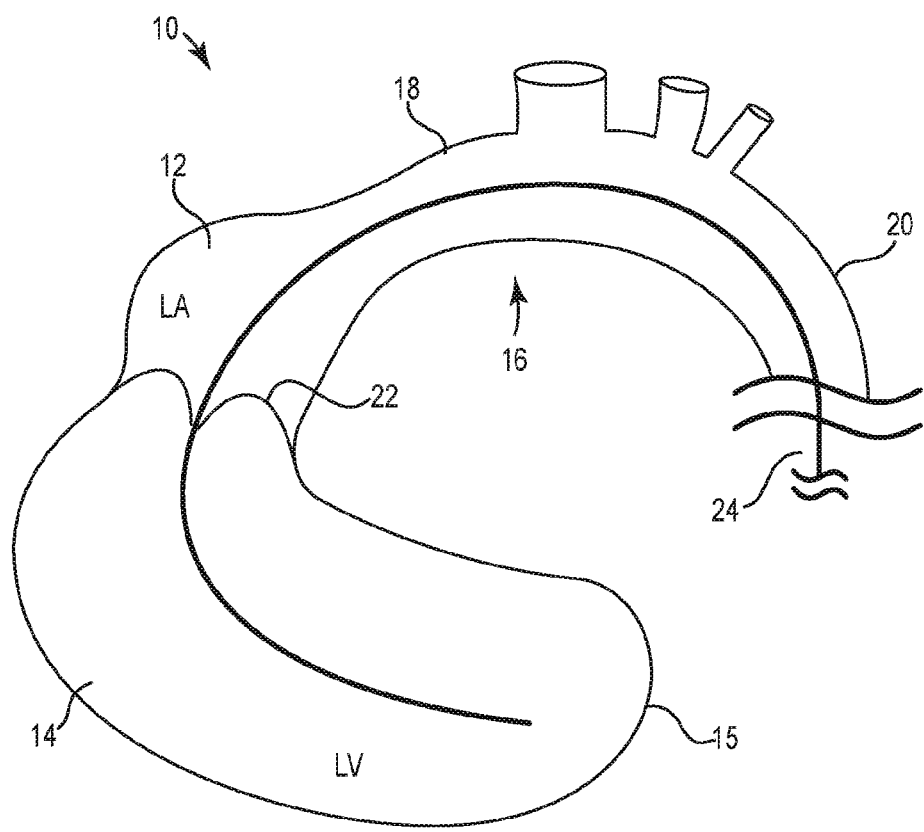
FIG. 1 is a schematic view of a method in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The invention pertains to techniques for gaining access to the interior of the heart. Once access has been gained to the interior of the heart, a variety of useful procedures may be performed. For illustrative purposes, embodiments of the invention will be described with respect to cardiac valve replacement. In some embodiments, the invention pertains to aortic valve replacement techniques that combine elements of percutaneous implantation methods and elements of surgical implantation methods. In some embodiments, aortic valve replacement may include a transapical approach.

In some embodiments, as illustrated in FIGS. 1-11, aortic valve replacement may involve a dual transapical procedure in which a transfemoral approach is used to reach the apex of the patient's heart from inside the left ventricle while a minimally invasive surgical procedure provides access to the exterior of the apex via an intercostal approach. In some embodiments, the Seldinger technique may be used to access the interior of the left ventricle.

FIGS. 1 through 5 illustrate the transfemoral portion of the dual transapical procedure. FIG. 1 illustrates a portion of the left heart 10. The left heart 10 includes the left atrium 12, the left ventricle 14 and the aorta 16. The aorta 16 may be considered as including an ascending aorta 18 and a descending aorta 20. An aortic valve 22 is disposed between the left atrium 12 and the left ventricle 14. The left ventricle 14 includes an apex 15. As seen in FIG. 1, a guidewire 24 has been advanced up through the descending aorta 20, through the ascending aorta 18 and through the aortic valve 22 into the left ventricle 14. In some embodiments, the guidewire 24 may access the vasculature via the femoral artery (not illustrated). In some embodiments, the guidewire 24 may instead access the vasculature via a radial or brachial artery (not illustrated) or through the aorta 16. In some embodiments, the guidewire 24 may include a trilobe centering balloon such as that shown in FIG. 8 of U.S. Patent Publication US 2008/0147180, which is incorporated by reference herein in its entirety.

Figure 2:
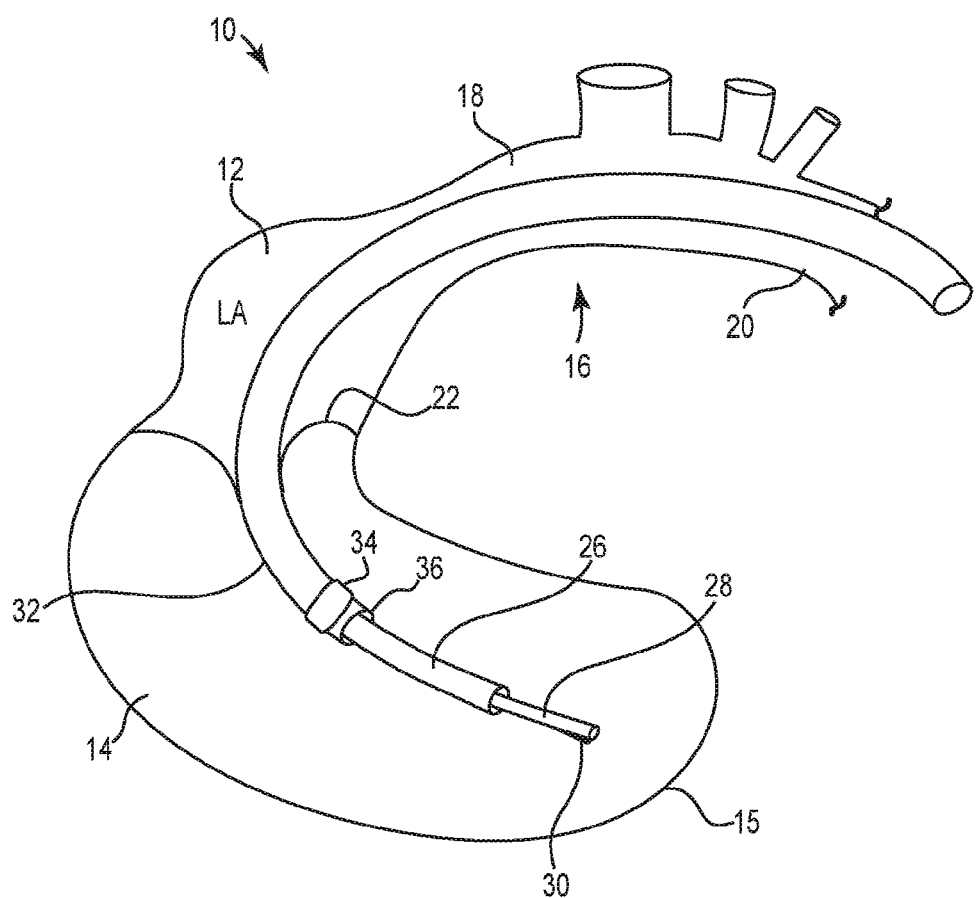
FIG. 2 is a schematic view of a method in accordance with an embodiment of the present invention.

Once the guidewire 24 has been placed, additional elements such as a guide catheter may be advanced over the guidewire 24 such that the guide catheter passes through the aorta 16, through the aortic valve 22 and into the left ventricle 14 to a location proximate the apex 15. In some embodiments, the guidewire 24 may be withdrawn once the guide catheter 26 has been placed. As seen in FIG. 2, a guide catheter 26 has been advanced over the guidewire 24, and the guidewire 24 has been withdrawn.

In some embodiments, a cutting element may be introduced through the guide catheter 26. The cutting element may be an elongate hollow needle. In some embodiments, as illustrated in FIG. 2, the cutting element may be a cutting catheter 28 that includes a blade 30 that is secured to the cutting catheter 28. By advancing the cutting catheter 28 through the guide catheter 26, the vasculature and the cardiac anatomy are protected from potential inadvertent damage that could otherwise be caused by the blade 30.

Before the cutting catheter 28 is advanced into significant contact with the myocardium, a balloon catheter 32 may be advanced over or through the guide catheter 26. In some embodiments, as illustrated, the balloon catheter 32 may be advanced over the guide catheter 26. In some embodiments, the balloon catheter 32 includes an inflatable balloon 34 disposed at or near a distal end 36 of the balloon catheter 32. In some embodiments (not illustrated), the guide catheter 26 itself includes an inflatable balloon and thus functions as a balloon catheter. In some embodiments, the balloon catheter 32 may be advanced over the cutting catheter 28, particularly if the cutting catheter 28 includes a configuration in which the blade 30 is withdrawn, retracted, folded or otherwise temporarily rendered inert to permit the balloon catheter 32 to advance over the cutting catheter 28. The balloon catheter 32 will include an inflation lumen (not shown) that permits inflation fluid to be communicated to an interior of the inflatable balloon 34 in order to inflate the inflatable balloon 34.

In FIG. 2, the guide catheter 26 is illustrated as extending distally beyond the balloon catheter 32. The cutting catheter 28 is illustrated as extending distally beyond the guide catheter 26. These relative positions are intended merely to be illustrative by showing each of the components in a single drawing but are not intended to describe or suggest any potential limitation regarding the relative positions of each of these components.

Figure 3:
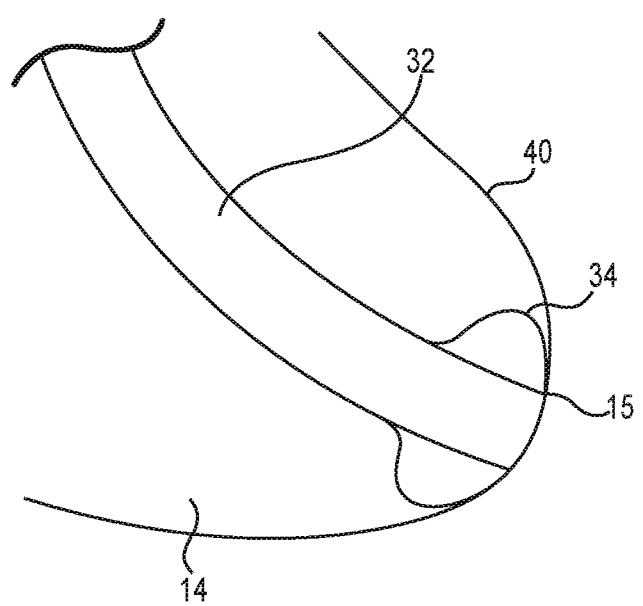
FIG. 3 is a schematic view of a method in accordance with an embodiment of the present invention.
Figure 4:
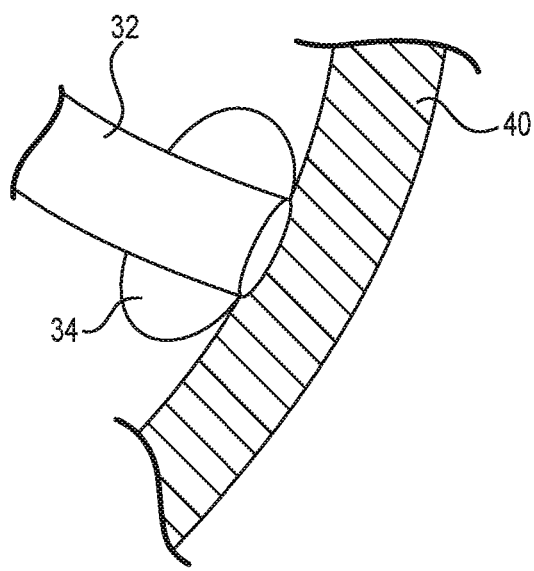
FIG. 4 is a schematic view of a method in accordance with an embodiment of the present invention.
Figure 5:
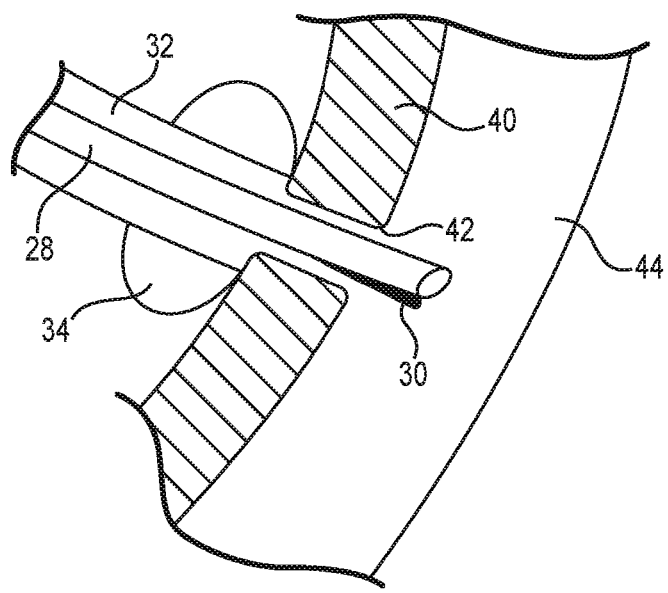
FIG. 5 is a schematic view of a method in accordance with an embodiment of the present invention.

In some embodiments, as illustrated in FIG. 3, the balloon catheter 32 (or other catheter optionally carrying an inflatable balloon, such as the guide catheter 26) may be advanced towards the apex 15 such that the inflatable balloon 34 is proximate the apex 15. The inflatable balloon 34 may be inflated to provide an air/fluid seal between the balloon catheter 32 and the heart wall such that little to no air may enter the heart and such that little or no blood may exit the heart. FIG. 4 is a cross-sectional view illustrating the position of the balloon catheter 32 relative to the heart wall 40. Once the inflatable balloon 34 has been inflated to provide an air/fluid seal between the balloon catheter 32 and the heart wall 40, and as seen in FIG. 5, the cutting catheter 28 may be advanced up to and through the heart wall 40 to form an aperture 42 that extends through the heart wall 40 and into the pericardial sac 44.

Figure 6:
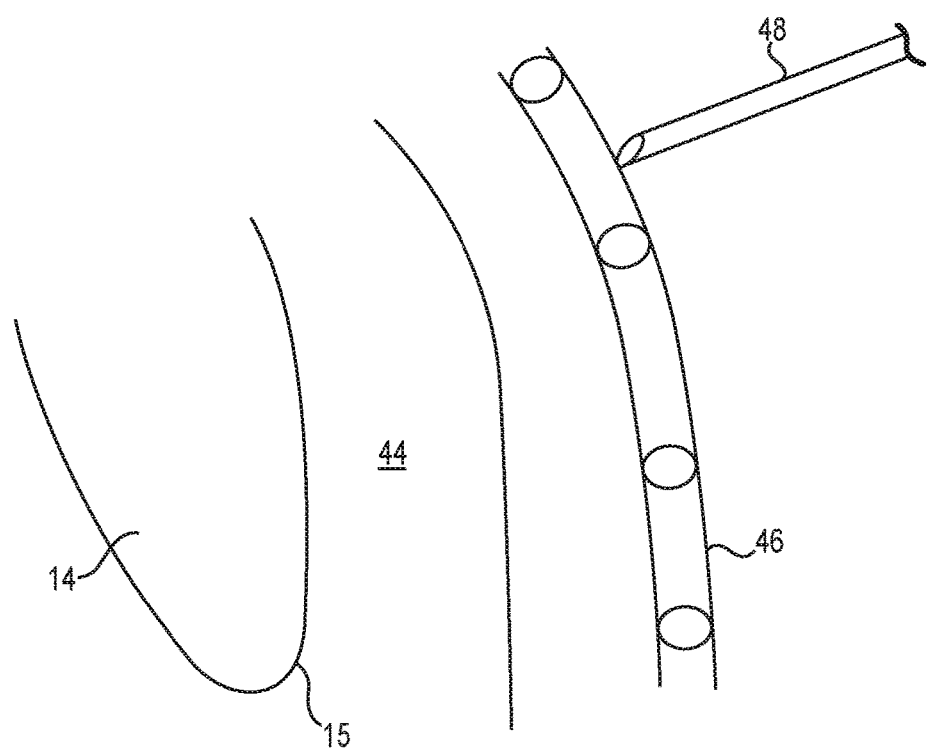
FIG. 6 is a schematic view of a method in accordance with an embodiment of the present invention.

In some embodiments, the dual transapical procedure also includes an intercostal portion of the procedure, as outlined in FIGS. 6 through 11. FIG. 6 shows the left ventricle 14 and apex 15 relative to the pericardial sac 44 and the ribcage 46. The intercostal portion of the procedure begins, in some embodiments, by penetrating the chest wall through the ribcage 46 using a hollow needle 48. In some embodiments, the ribcage 46 is penetrated through the 4$^{th}$ intercostal space or the 5$^{th}$ intercostal space. In some embodiments, the ribcage 46 is penetrated at a relative level that is above the normal position of the apex 15.

Figure 7:
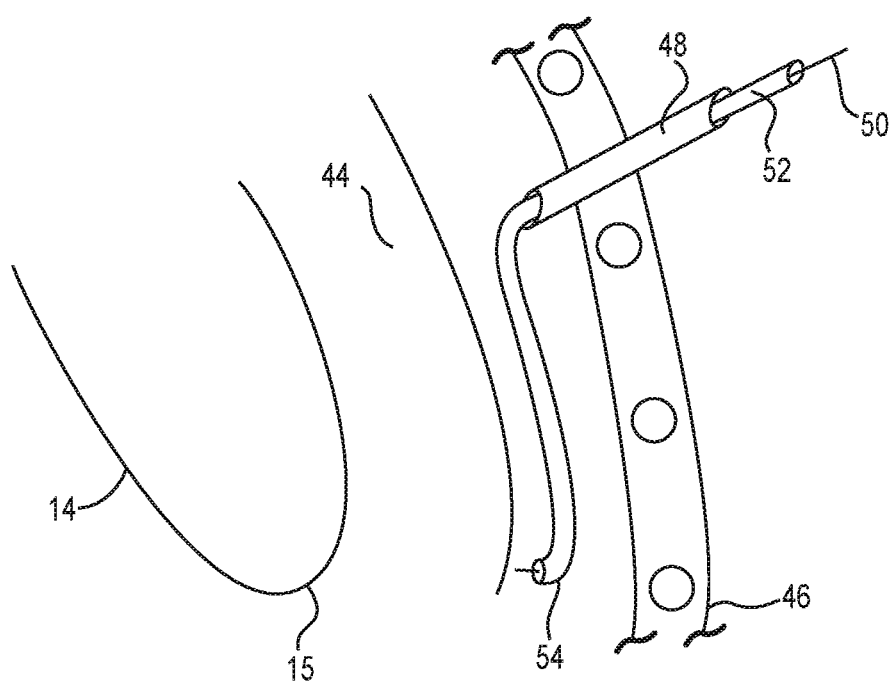
FIG. 7 is a schematic view of a method in accordance with an embodiment of the present invention.

As seen in FIG. 7, the hollow needle 48 has penetrated the ribcage 46 and a guidewire 50 has been advanced through the hollow needle 48 and down through the space between the pericardial sac 44 and the ribcage 46 to a position proximate (but exterior to the pericardiac sac 44) to the apex 15. Once the guidewire 50 has been placed, a malleable S-shaped catheter 52 is advanced over the guidewire 50. In some embodiments, the S-shaped catheter 52 is formed of a shape memory material such as a shape memory polymer or a shape memory metal. It can be seen that a distal end 54 of the S-shaped catheter 52 is at a position that is relatively lower than the point at which the hollow needle 48 penetrated the ribcage 46.

Figure 8:
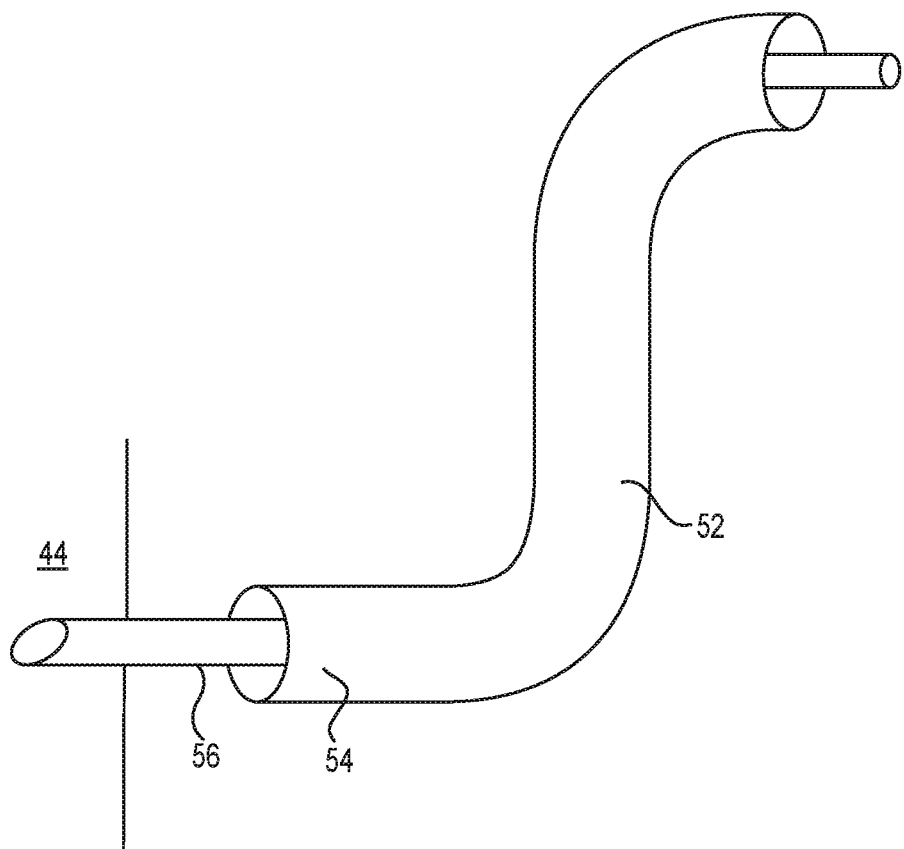
FIG. 8 is a schematic view of a method in accordance with an embodiment of the present invention.

As seen in FIG. 8, a hollow needle 56 may be advanced over the guidewire 50 or through the S-shaped catheter 52 (if the guidewire 50 has already been withdrawn) and penetrates the pericardial sac 44. At this point, the distal end 54 of the S-shaped catheter 52 is proximate a distal end of either the guide catheter 26, the cutting catheter 28 and/or the balloon catheter 32. In some embodiments (not illustrated), a separate balloon catheter 58 including an inflatable balloon 60 is advanced through the guide catheter 26 to a position proximate the distal end 54 of the S-shaped catheter 52.

Figure 9:
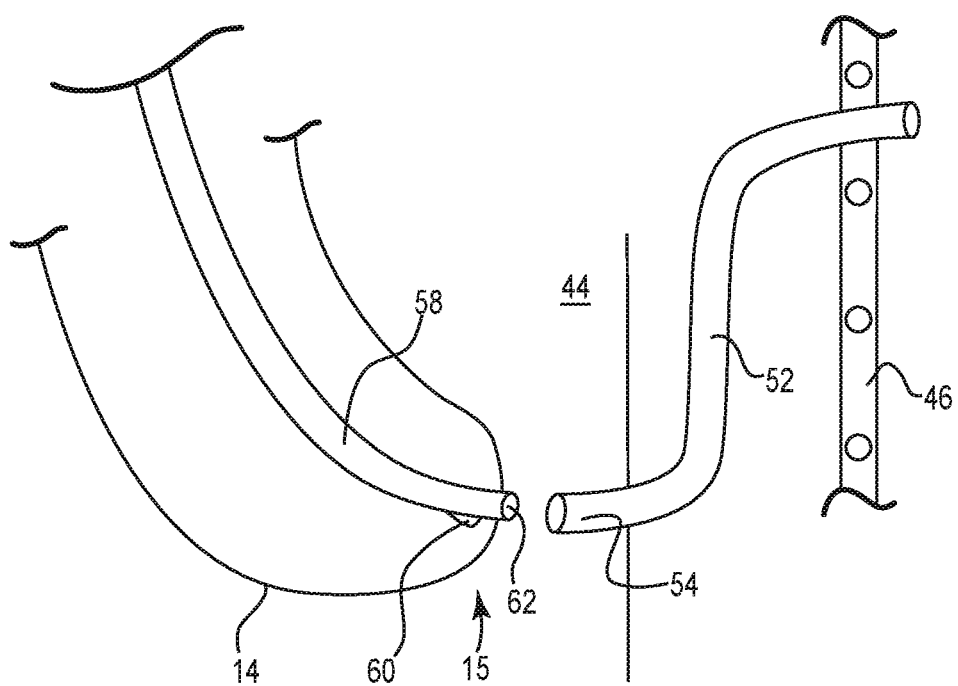
FIG. 9 is a schematic view of a method in accordance with an embodiment of the present invention.

Turning now to FIG. 9, the distal end 54 of the S-shaped catheter 52 is proximate a distal end 62 of the balloon catheter 58. In some embodiments, the distal end 54 of the S-shaped catheter 52 is configured to capture the distal end 62 of the balloon catheter 58 such that the S-shaped catheter 52 may be withdrawn proximally in order to pull the distal end 62 of the balloon catheter 58. In some embodiments, magnets may be used to secure the catheters 52 and 58 together. In some embodiments, there may be a frictional fit between the two.

Figure 10:
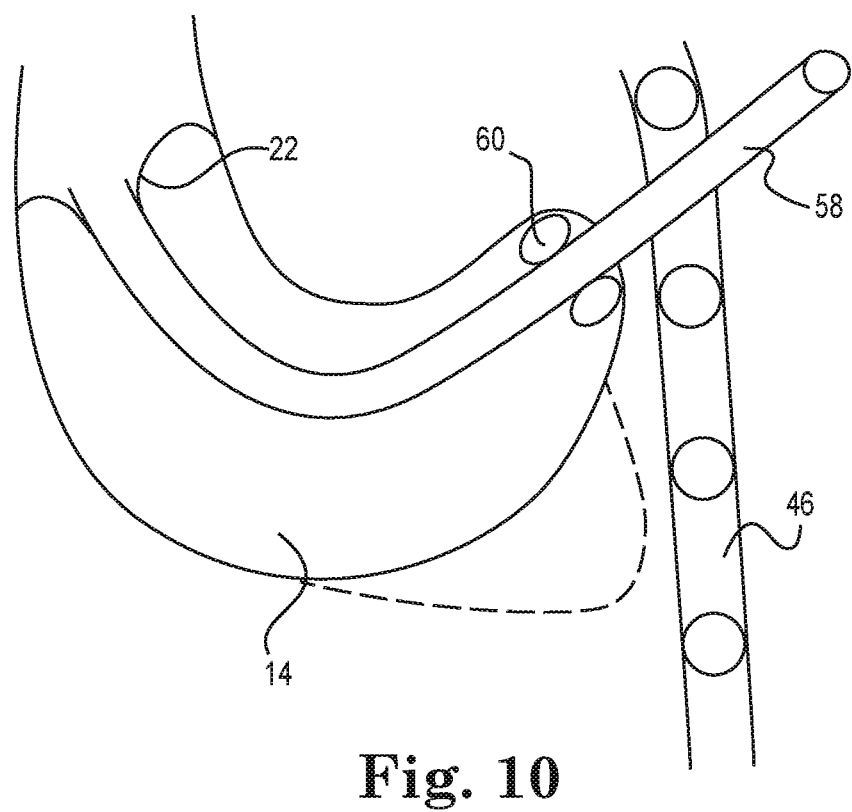
FIG. 10 is a schematic view of a method in accordance with an embodiment of the present invention.

As seen in FIG. 10, the inflatable balloon 60 may be inflated such that pulling on the balloon catheter 58 causes the apex 15 of the left ventricle 14 to be lifted. In some embodiments, the inflatable balloon 60 may be configured differently and may be stronger than, for example, the inflatable balloon 34 that was used to provide an air/fluid seal. The balloon catheter 58 may be withdrawn proximally a sufficient distance to lift the apex 15 of the left ventricle 14 to a position that is aligned or substantially aligned with the initial puncture through the ribcage 46. The native position of the left ventricle 14 is shown in phantom, illustrating how the left ventricle 14 has been lifted. It will be appreciated that this method provides easy access from a position exterior the chest wall to the aortic valve 22.

Figure 11:
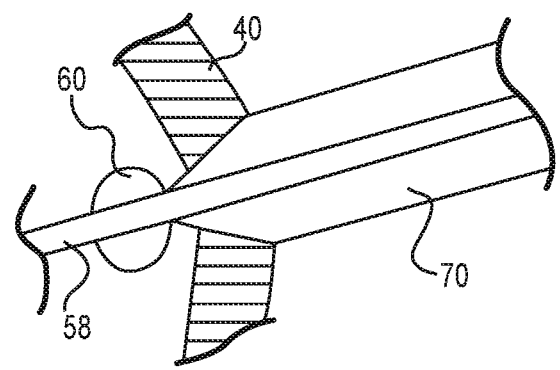
FIG. 11 is a schematic view of a method in accordance with an embodiment of the present invention.

As seen in FIG. 11, a port 70 may be advanced over the balloon catheter 58 to provide access for delivery and deployment of a replacement aortic valve (not shown in this Figure). In some embodiments, the inflatable balloon 60 may be deflated before the port 70 is advanced over the balloon catheter 58 into the left ventricle 14.

Figure 12:
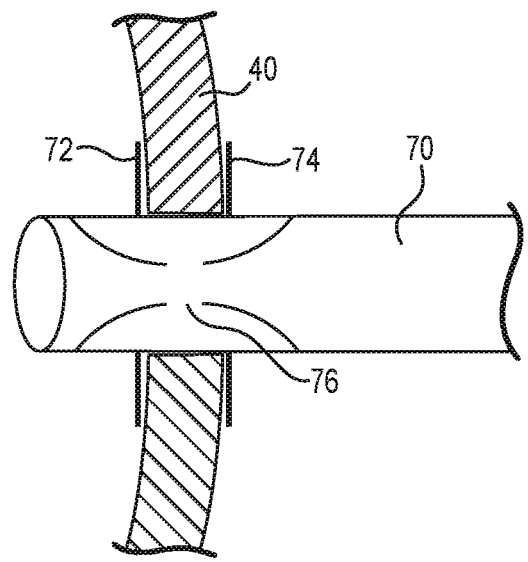
FIG. 12 is a schematic view of a method in accordance with an embodiment of the present invention.

In some embodiments, as illustrated in FIG. 12, the port 70 may include structure that helps to secure the port 70 relative to the heart wall 40 and to prevent air from passing through port 70 into the heart and/or prevent blood from leaking out of the heart. This is particularly useful when the procedures described herein are undertaken off-pump, i.e., with a beating heart. In some embodiments, the port 70 includes an inner flange 72 and an outer flange 74. The inner flange 72 and the outer flange 74 may be resilient annular structures that help to secure the port 70 relative to the heart wall 40. In some embodiments, the inner flange 72 and the outer flange 74 may be sufficiently resilient to lay flat against the port 70 for delivery of the port 70 into the heart wall 40. In some embodiments, the port 70 includes a valve 76 such as a hemostasis valve that permits delivery through the valve 76 while preventing air and blood from leaking in either direction through the valve 76.

Figure 13:
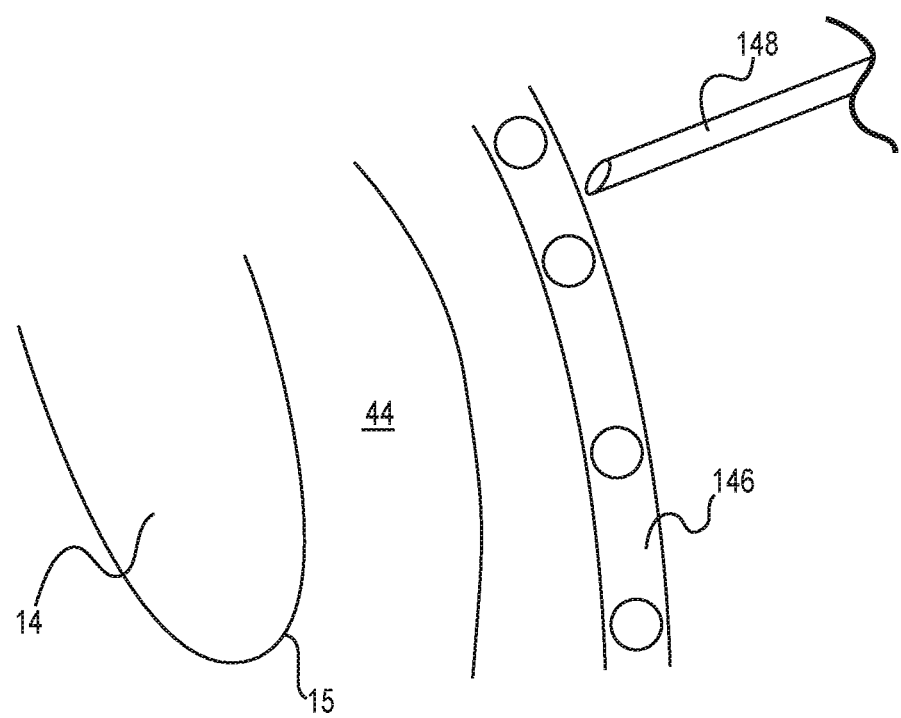
FIG. 13 is a schematic view of a method in accordance with an embodiment of the present invention.

In some embodiments, access to the aortic valve 22 may be provided without the transfemoral or percutaneous portion of the procedure. In some embodiments, the steps shown in FIGS. 1-5 and 9 may be excluded. Another method of providing access to the aortic valve 22 is illustrated in FIGS. 13-18. FIG. 13 shows the left ventricle 14 and apex 15 relative to the pericardial sac 44 and the ribcage 46. The intercostal portion of the procedure begins, in some embodiments, by penetrating the chest wall through the ribcage 46 using a hollow needle 148. In some embodiments, the ribcage 46 is penetrated through the 4$^{th}$ intercostal space or the 5$^{th}$ intercostal space. In some embodiments, the ribcage 46 is penetrated at a relative level that is above the normal position of the apex 15.

Figure 14:
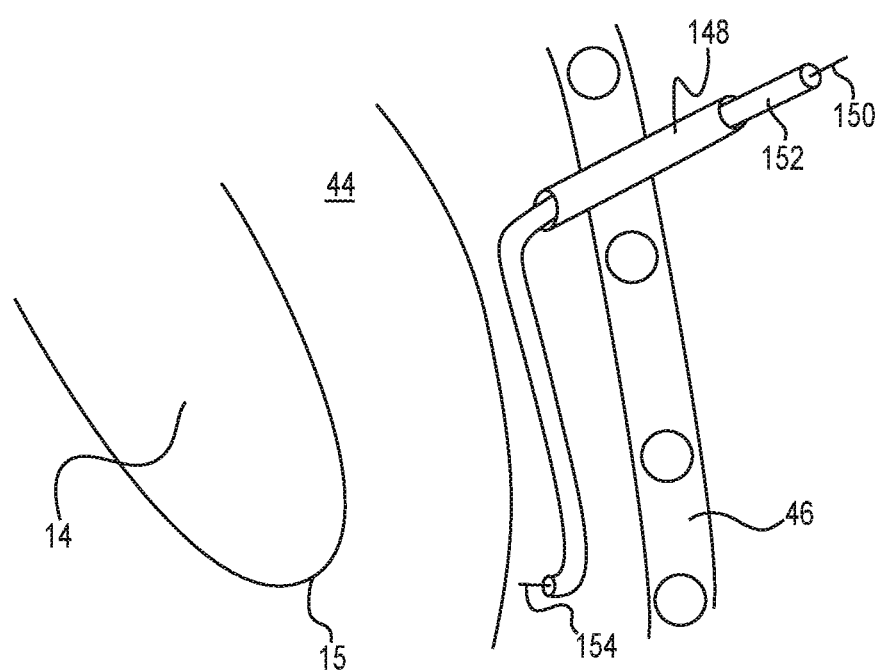
FIG. 14 is a schematic view of a method in accordance with an embodiment of the present invention.

As seen in FIG. 14, the hollow needle 148 has penetrated the ribcage 46 and a guidewire 150 has been advanced through the hollow needle 148 and down through the space between the pericardial sac 44 and the ribcage 46 to a position proximate (but exterior to the pericardiac sac 44) to the apex 15. Once the guidewire 150 has been placed, a malleable S-shaped catheter 152 is advanced over the guidewire 150. In some embodiments, the S-shaped catheter 52 is formed of a shape memory material such as a shape memory polymer or a shape memory metal. It can be seen that a distal end 154 of the S-shaped catheter 152 is at a position that is relatively lower than the point at which the hollow needle 48 penetrated the ribcage 46.

Figure 15:
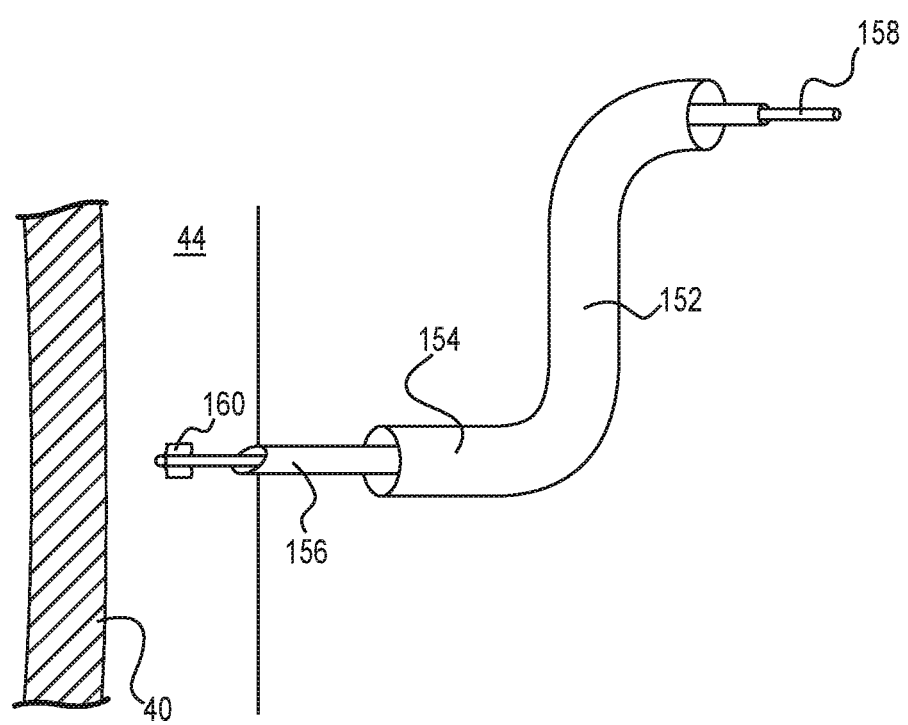
FIG. 15 is a schematic view of a method in accordance with an embodiment of the present invention.

As seen in FIG. 15, a hollow needle 156 may be advanced over the guidewire 150 or through the S-shaped catheter 152 (if the guidewire 150 has already been withdrawn) and penetrates the pericardial sac 44. In some embodiments, a balloon catheter 158 having an inflatable balloon 160 may be advanced through the S-shaped catheter 152. As the hollow needle 156 penetrates through the pericardial sac 44 and the heart wall 40, the balloon catheter 158 may be advanced through the resulting aperture and the inflatable balloon 160 may be inflated inside the left ventricle 14 in order to provide an air/fluid seal. In some embodiments, a second inflatable balloon (not illustrated) may be disposed just outside the heart wall 40 and may be inflated to further seal against air and/or blood.

Figure 16:
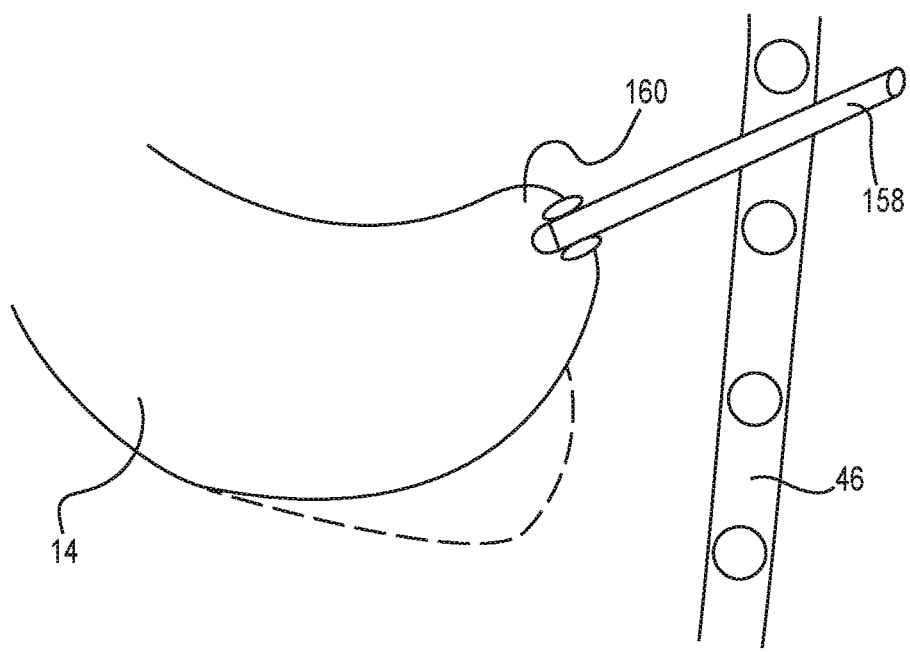
FIG. 16 is a schematic view of a method in accordance with an embodiment of the present invention.

In some embodiments, as illustrated in FIG. 16, the inflatable balloon 160 may be inflated such that pulling on the balloon catheter 158 causes the apex 15 of the left ventricle 14 to be lifted. The balloon catheter 158 may be withdrawn proximally a sufficient distance to lift the apex 15 of the left ventricle 14 to a position that is aligned or substantially aligned with the initial puncture through the ribcage 46. The native position of the left ventricle 14 is shown in phantom, illustrating how the left ventricle 14 has been lifted. It will be appreciated that this method provides easy access from a position exterior the chest wall to the aortic valve 22.

Figure 17:
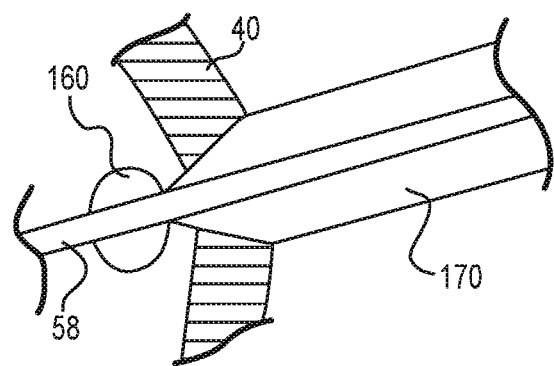
FIG. 17 is a schematic view of a method in accordance with an embodiment of the present invention.

As seen in FIG. 17, a port 170 may be advanced over the balloon catheter 158 to provide access for delivery and deployment of a replacement aortic valve (not shown in this Figure). In some embodiments, the inflatable balloon 160 may be deflated before the port 170 is advanced over the balloon catheter 158 into the left ventricle 14.

Figure 18:
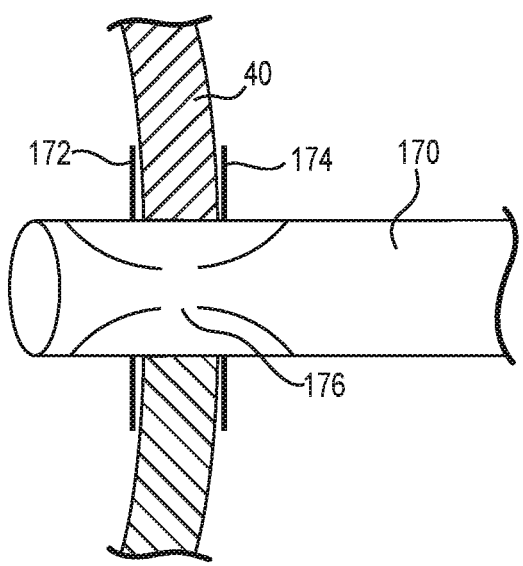
FIG. 18 is a schematic view of a method in accordance with an embodiment of the present invention.

In some embodiments, as illustrated in FIG. 18, the port 170 may include structure that helps to secure the port 170 relative to the heart wall 40 and to prevent air from passing through port 170 into the heart and/or prevent blood from leaking out of the heart. This is particularly useful when the procedures described herein are undertaken off-pump, i.e., with a beating heart. In some embodiments, the port 170 includes an inner flange 172 and an outer flange 174. The inner flange 172 and the outer flange 174 may be resilient annular structures that help to secure the port 170 relative to the heart wall 40. In some embodiments, the inner flange 172 and the outer flange 174 may be sufficiently resilient to lay flat against the port 170 for delivery of the port 170 into the heart wall 40. In some embodiments, the port 170 includes a valve 176 such as a hemostasis valve that permits delivery through the valve 176 while preventing air and blood from leaking in either direction through the valve 176.

Figure 19:
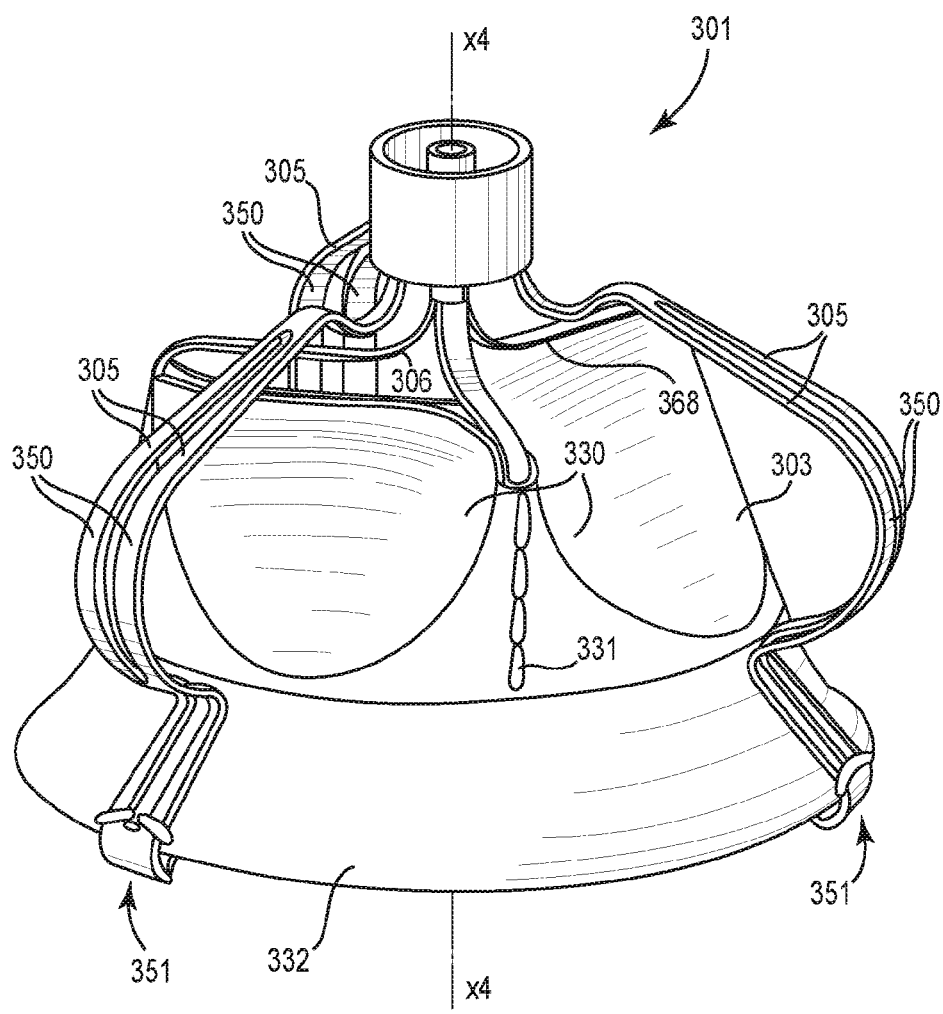
FIG. 19 is a perspective view of an embodiment of an implantable prosthetic aortic valve.

Once the port 70 (or 170) has been deployed, a variety of different valves, including prosthetic aortic valves, may be implanted through the port 70 (170). An illustrative but non-limiting example of a suitable prosthetic valve may be seen in FIG. 19. FIG. 19 illustrates a valve 301 that can be implanted in a variety of ways, including a minimally invasive procedure. The valve 301 includes an armature 302 and a set of leaflets 303. The armature 302 has a general cage-like structure that includes a number of ribs extending along an axis X4. The ribs include a first series of ribs 305 and a second series of ribs 306. The ribs 305, 306 may be made of a radially expandable metal. In some embodiments, the ribs 305, 306 may be formed of a shape memory material such as Nitinol.

The first series of ribs 305 and the second series of ribs 306 have different functions. In some embodiments, the ribs 305 form an external or anchor portion of the armature 302 that is configured to enable the location and anchorage of the valve 301 at an implantation site. The ribs 306 are configured to provide an internal or support portion of the armature 302. In some embodiments, the ribs 306 support a plurality of valve leaflets 330 provided within the set of leaflets 303.

In some embodiments, the ribs 305 are arranged in sets of ribs (threes or multiples of three) such that they are more readily adaptable, in a complementary way, to the anatomy of the Valsalva's sinuses, which is the site of choice for implantation of the valve 301. The Valsalva's sinuses are the dilatations, from the overall lobed profile, which are present at the root of the aorta, hence in a physiologically distal position with respect to the aortic valve annulus.

In some embodiments, the structure and the configuration of the ribs 306 is, as a whole, akin to that of the ribs 305. In the case of the ribs 306, which form the internal part of the armature 302 of the valve 301, there is, however, usually the presence of just three elements that support, in a position corresponding to homologous lines of commissure (which take material form as sutures 331), on the valve leaflets 330. Essentially, the complex of ribs 306 and valve leaflets 330 is designed to form the normal structure of a biological valve prosthesis. This is a valve prosthesis which (in the form that is to be implanted with a surgical operation of a traditional type, hence of an invasive nature) has met with a wide popularity in the art.

In some embodiments, suitable materials used to form the leaflets 330, such as the pericardium or meningeal tissue of animal origin are described for example in EP 0 155 245 B and EP 0 133 420 B, both of which are hereby incorporated by reference herein in their entirety. In some embodiments, the valve 301 may be similar to those described in U.S. Patent Publication No. 2005/0197695, which is hereby incorporated by reference herein in its entirety.

Figure 20:
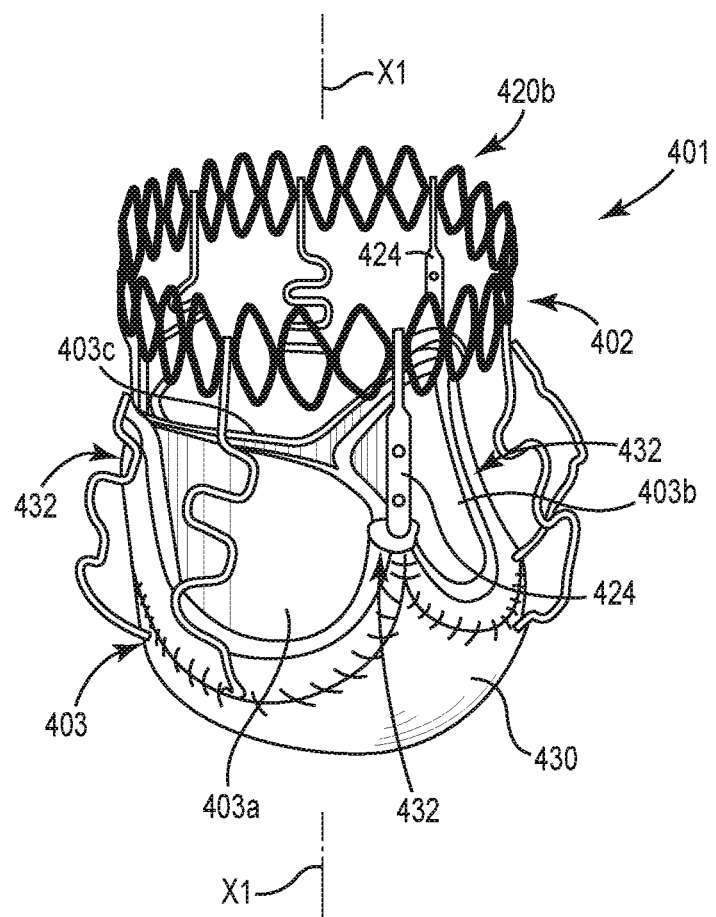
FIG. 20 is a perspective view of an embodiment of an implantable prosthetic aortic valve.

Another illustrative but non-limiting example of a suitable prosthetic valve may be seen in FIG. 20. FIG. 20 illustrates a prosthetic valve 401 that can be implanted using a variety of different techniques. In some embodiments, the valve 401 may be implanted using a minimally invasive procedure such as those discussed herein. As illustrated, the valve 401 includes an armature 402 and a valve sleeve 403 that is coupled to the armature 402 and that includes three valve leaflets 403a, 403b and 403c.

As can be seen, the armature 402 has a general cage-like structure and is generally symmetric about a principal axis X1. As shown, the armature 402 defines a lumen which operates as a flow tube or duct to accommodate the flow of blood there through. As will be readily apparent to those skilled in the art, a major characteristic of the present invention is the absence of structural elements that can extend in the lumen through which blood flows.

The valve sleeve 403 may be constructed according to various techniques known in the art. For example, in some embodiments, techniques for the formation of the valve leaflets, assembly of the valve sleeve and installation thereof on an armature that can be used in the context of the present disclosure are described in EP-A-0 133 420, EP-A-0 155 245 and EP-A-0 515 324 (all of which are hereby incorporated by reference). In some embodiments, the valve 401 may be similar to those described in U.S. Patent Publication No. 2006/0178740, which is hereby incorporated by reference herein in its entirety.

As will be understood by those of ordinary skill in the art, in operation, the valve leaflets 403a, 403b, 403c are able to undergo deformation, divaricating and moving up against the armature 402 so as to enable free flow of the blood through the prosthesis. When the pressure gradient, and hence the direction of flow, of the blood through the prosthesis tends to be reversed, the valve leaflets 403a, 403b, 403c then move into the position represented in FIG. 20, in which they substantially prevent the flow of the blood through the prosthesis. In some embodiments, the valve leaflets 403a, 403b, 403c are made in such a way as to assume spontaneously, in the absence of external stresses, the closed configuration represented in FIG. 20.

The prosthetic valves described herein, such as the valve 301 and the valve 401, may be delivered in a variety of different manners. In some embodiments, a prosthetic valve may be delivered in a minimally invasive manner in which the valve is disposed on a delivery apparatus that is configured to be inserted into the patient through the port 70 (170) discussed above. Once the prosthetic valve has been appropriately positioned, the delivery apparatus can be manipulated to deploy the valve.

An illustrative but non-limiting example of a suitable delivery device can be seen in FIGS. 21A and 21B, which are schematic illustrations of a delivery device 501. In the illustrated embodiment, the delivery device 501 includes a carrier portion 502 for enclosing and carrying a prosthetic device (not visible in this view) and a manipulation portion 503 that couples the carrier portion 502 to a control handle 504. The control handle 504 includes several actuator members such as the sliders 505 and 506. In some embodiments, an optional third actuator member may be provided for controlling translational movement of the carrier portion 502 relative to the control handle 504. As will be appreciated, this feature permits microadjustment of the carrier portion 502 and the valve prosthesis in relation to a desired location while the control handle 504 is in a fixed location. A further optional actuator on the control handle 504 provides rotational adjustment of carrier portion 502 in relation to manipulation portion 50503 and/or control handle 4. This permits the optional placement of the valve prosthesis through at least 360 degrees of rotation.

The manipulation portion 503 may have more than one configuration. FIG. 21A shows a configuration in which the manipulation portion 503 is a substantially rigid bar having a length that permits positioning of the carrier portion 503, and hence the prosthetic valve disposed therein, at an aortic valve site. In some embodiments, the substantially rigid bar may have a length of about 10 centimeters. The delivery device 501 is sized and dimensioned to permit easy surgical manipulation of the entire instruction as well as the actuators on the instrument without contacting parts of the subject in a way to interfere with the user's position of the valve prosthesis.

FIG. 21B illustrates an embodiment in which the manipulation portion 503 is an elongated, flexible catheter-like member that can be used for transvascular catherization. However, this embodiment can be used in the procedures discussed herein. In some embodiments, the catheter-like member is braided or is otherwise configured to facilitate torque transmission from the control handle 504 to the carrier portion 502 such that the operator may effect radial positioning of the carrier portion 502 during the implantation procedure.

Figure 22:
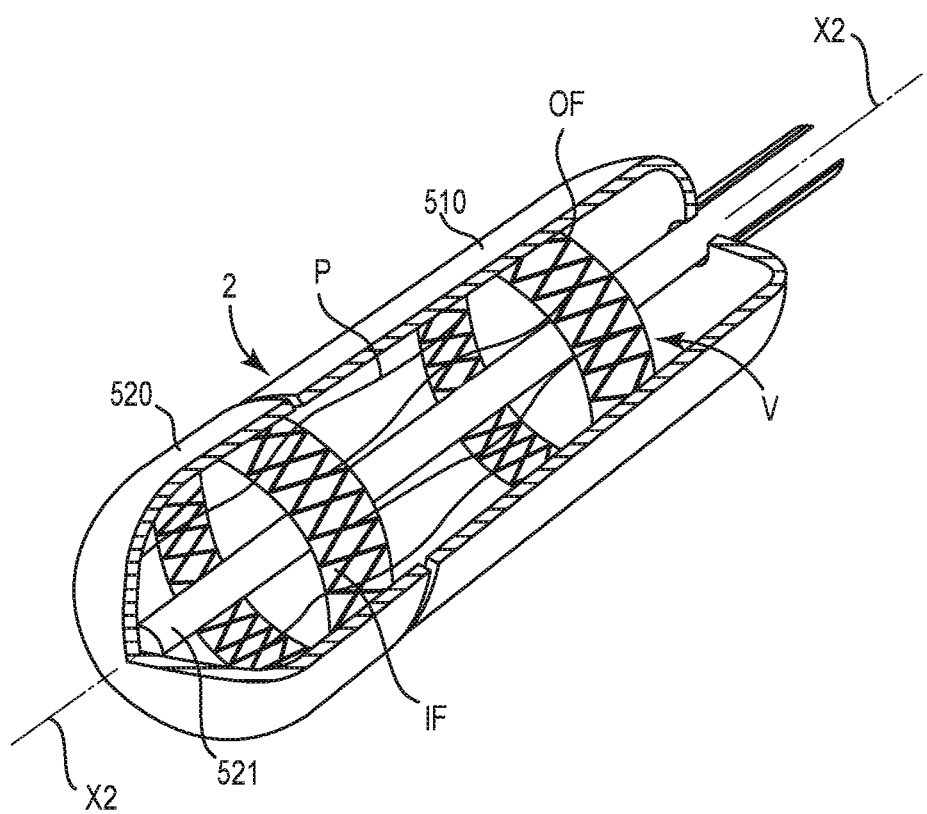
FIG. 22 is a partial cross-section of the delivery device shown in FIGS. 21A and 21B.

As shown in FIG. 22, the carrier portion 502 includes two deployment elements 510 and 520, each of which are independently operable to allow the expansion of at least one corresponding, radially expandable portion of the valve prosthesis V. In some embodiments, the valve prosthesis V may be self-expanding or may require expansion by another device (such as, for example, balloon expansion).

In the illustrated embodiment, the valve prosthesis V is self-expanding, and is arranged within the carrier portion 502 such that an expandable portion IF and an expandable portion OF are each located within one of the deployment elements 510, 520. Each deployment element 510, 520 may be formed as a collar, cap or sheath. In yet a further embodiment, the elements 510, 520 are porous (or have apertures) such that blood flow is facilitated prior, during and after placement of prosthesis V. As will be appreciated, blood flows through the elements 510, 520 and over or through the prosthesis V during the placement procedure. Each deployment element 510, 520 is able to constrain the portions IF, OF in a radially contracted position, against the elastic strength of its constituent material. The portions IF, OF are able to radially expand, as a result of their characteristics of superelasticity, only when released from the deployment element 510, 520. Typically, the release of the portions IF, OF is obtained by causing an axial movement of the deployment elements 510, 520 along the main axis X2 of the carrier portion 502. In one embodiment, the operator causes this axial movement by manipulating the sliders 505 and 506, which are coupled to the deployment elements 510, 520. In some embodiments, suitable delivery devices such as the delivery device 501 may be found in U.S. Patent Publication No. 2008/0147182, which is hereby incorporated by reference herein in its entirety.

Figure 23:
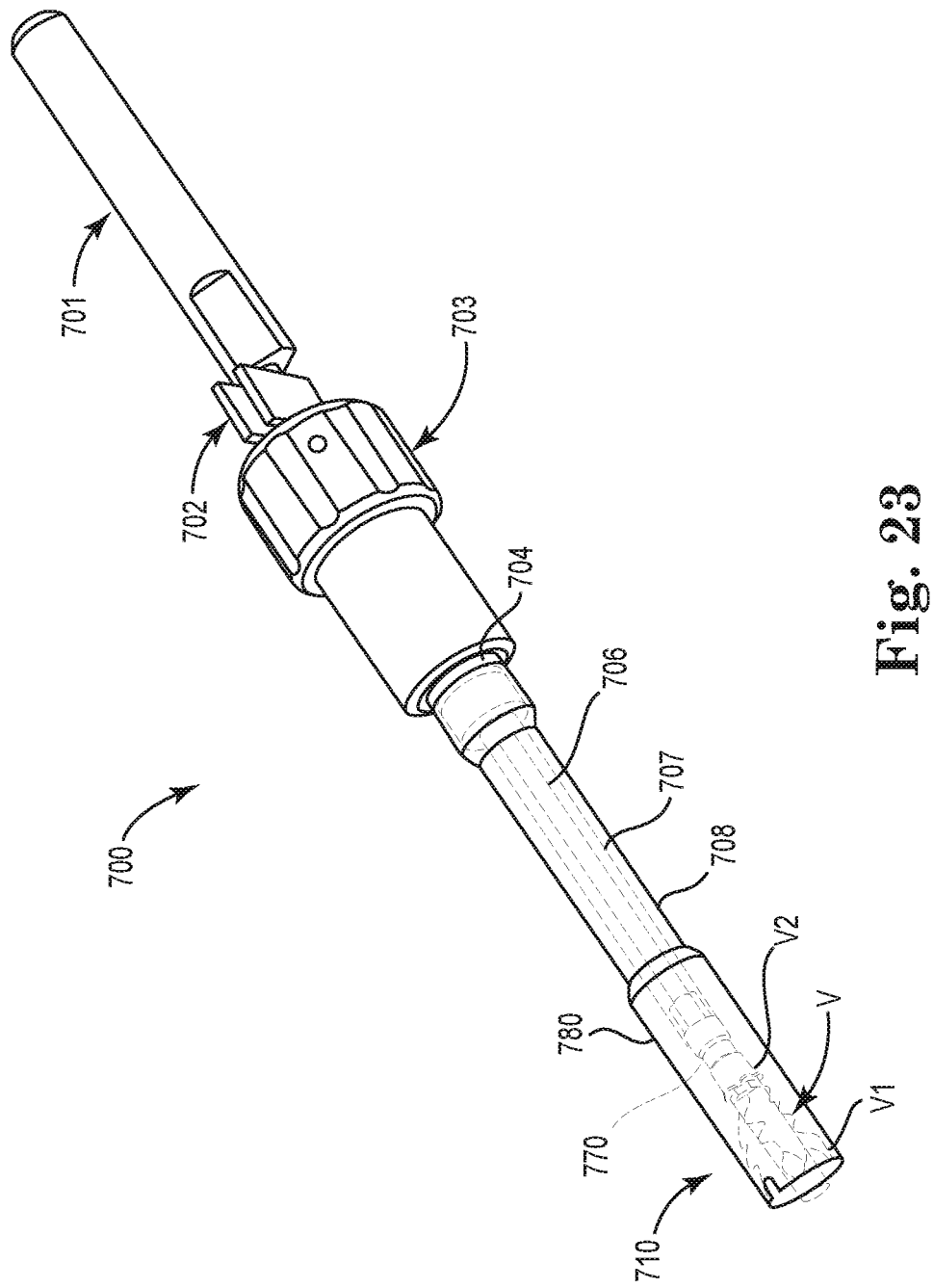
FIG. 23 is a schematic illustration of an embodiment of a delivery device.

Another illustrative but non-limiting example of a delivery device may be seen in FIG. 23. FIG. 23 shows an prosthetic valve delivery device 700 that includes a handle 701 for manipulation by a practitioner and a holder unit 710 for a valve V to be delivered. In the illustrated embodiment, the handle 701 and the holder unit 710 are generally located at proximal and distal ends, respectively, of the device 700. In this, proximal refers to the portion of the device 700 manipulated by the practitioner while distal refer to the end of the device 700 at which the valve V is delivered.

In one embodiment, the valve V includes two annular end portions V1 and V2 and is arranged within the holder unit 710 at the distal delivery end of the device 700 with the annular portions V1, V2 in a radially contracted configuration. In some embodiments, the valve V is delivered by releasing the annular portion V1 first and then by causing the valve V to gradually expand (e.g. due to its elastic or superelastic nature), starting from the portion V1 and continuing to the portion V2, until expansion is complete.

Figure 24:
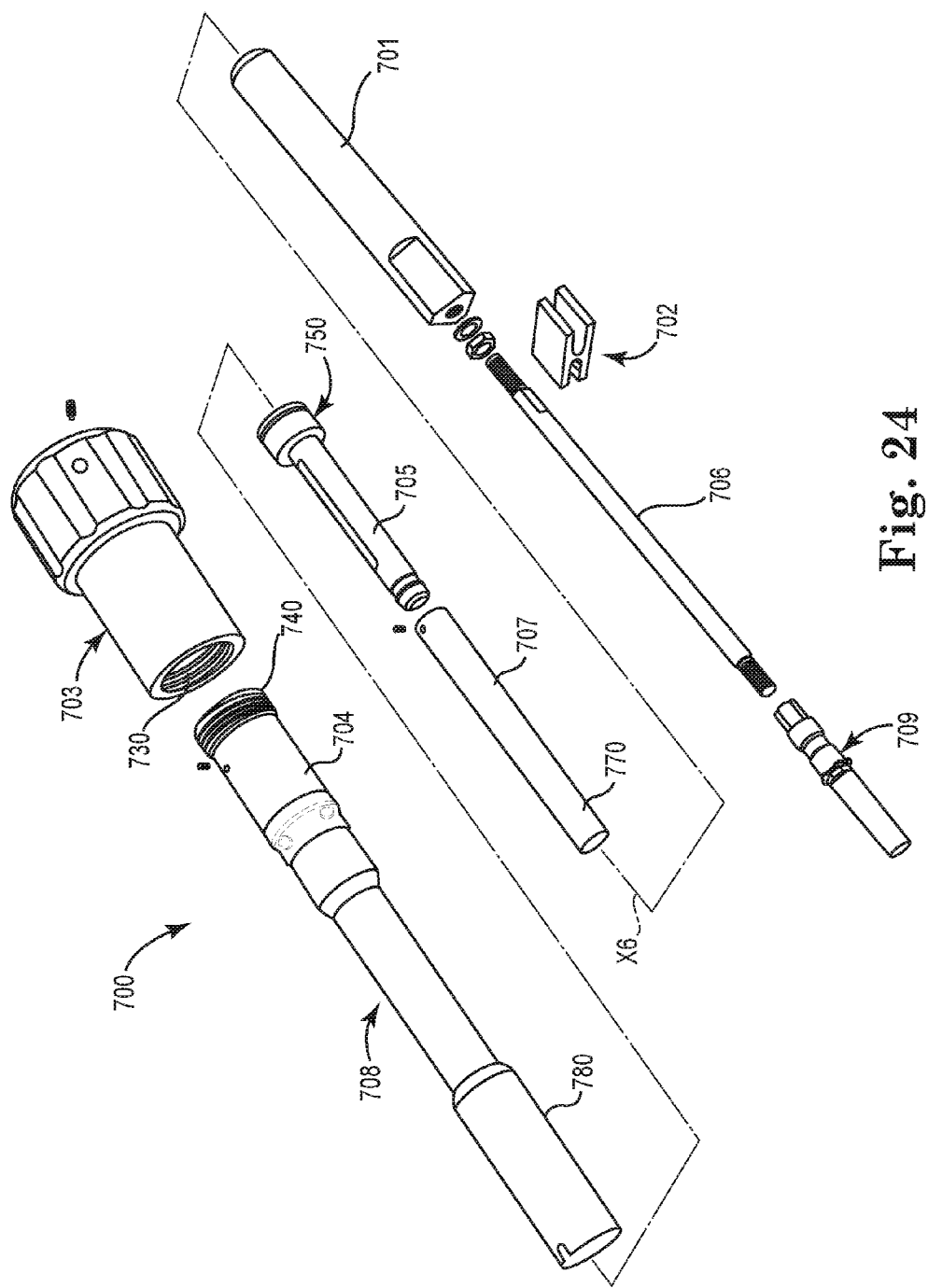
FIG. 24 is an exploded view of the delivery device of FIG. 23.

As shown in the exploded view of FIG. 24, a shaft 706 (which may be either rigid or flexible) extends from the handle 701 to the holder unit 710 for the valve. The holder unit 710 includes an annular groove or similar recessed 709 formation adapted to receive the (proximal) annular portion V2 of the valve V in a radially contracted condition. A tubular sheath or sleeve is slidably arranged over the shaft 706. Such a sleeve (hereinafter the "inner" sleeve) includes a proximal portion 705 proximate the handle 701 as well as a distal portion 707. The inner sleeve is of a length such that it can extend axially over the shaft 706 to form with its marginal end an intermediate tubular member 770 of the holder unit 710 which surrounds the formation 709 to radially constrain and retain the annular portion V2 of the valve V located therein.

In some embodiments, the proximal portion 705 of the inner sheet or sleeve terminates in an annular member 750 adapted to abut against a stop member 702. When in place on the shaft 706, the stop member 702 prevents the inner sleeve from being retracted (i.e. slid back) along the axis X6 of the shaft 706 from the position shown in FIG. 7, where the intermediate member or constraint 770 of the holder unit 710 radially constrains and retains the annular portion V2 of the valve V. When the stop member 702 is removed or otherwise disengaged, the inner sleeve can be retracted along the axis X6 so that the intermediate member 770 of the holder unit releases the annular portion V2 of the valve V.

In one embodiment, the stop or blocking member 702 includes a fork-shaped body (e.g. of plastics material) adapted to be arranged astride the root portion of the shaft 706 between the annular member 750 and the handle 701 to prevent "backward" movement of the inner sleeve towards the handle 701.

A further tubular sheet or sleeve (hereinafter the "outer" sleeve) is slidably arranged over the inner sleeve 705, 707. The outer sleeve 704 includes a proximal portion having an outer threaded surface 740 to cooperate with a complementary threaded formation 730 provided at the inner surface of a tubular rotary actuation member 703 arranged around the proximal portion 704 of the outer sleeves. In an embodiment, the actuation member 703 encloses the annular member 750 of the inner sleeve. The outer sleeve 704 extends over the inner sleeve 705, 707 and terminates with a distal portion 708 including an terminal constraint or outer member 780 adapted to extend around the distal portion to form an external tubular member of the holder unit 710 adapted to radially constrain and retain the annular portion V1 of the valve V located therein.

In some embodiments, the threaded surface/formations 730, 740 form a "micrometric" device actuatable by rotating the actuation member 703 to produce and precisely control axial displacement of the outer sleeve along the axis X6 of the shaft 706. Such a controlled movement may take place along the axis X6 of the shaft 706 starting from an extended position, as shown in FIG. 23, where the outer member 780 of the holder unit 710 radially constrains and retains the valve V. In these embodiments, which allow such a gradual movement or retraction, the outer member 780 gradually releases first the annular portion V1 of the valve V and then the remaining portions of the valve located between the annular portion V1 and the annular portion V2, thus permitting gradual radial expansion of the valve V.

In one embodiment, the retraction movement produced by the "micrometric" actuation device 730, 740 actuated via the rotary member 703 is stopped when the distal marginal end of the outer member 780 is aligned with the marginal end of the intermediate member 770 which still radially constrains and retains the annular portion V2 of the valve V in the formation 709. As further described below, in that condition, the valve V is partly expanded (i.e., more or less "basket-like") with the annular portion V1 completely (or almost completely) expanded and the annular portion V1 still contracted.

Starting from that position, if the stop member 702 is removed or otherwise disengaged, both the inner sleeve and the (retracted) outer sleeve mounted thereon can be slid back along the axis X6 towards the handle 701. In that way, the intermediate member 770 of the holder unit 710 releases the annular portion V2 of the valve V thus permitting valve expansion to become complete. Valve expansion is not hindered by the member 780 as this is likewise retracted towards the handle 701.

In an illustrative embodiment, the practitioner introduces the device 700 into the patient's body. In a particular example of aortic valve replacement, the device 700 may be placed such that the outer member 780 is located immediately distal (with respect to blood flow from the left ventricle) of the aortic annulus so that the annular portions V1 and V2 are located on opposite sides of the Valsalva sinuses.

One the device 700 is placed such that the outer member 780 is disposed properly at the annulus site, the rotary actuation member 730 may be actuated by rotating the rotary actuation member in such a way that cooperation of the threaded sections 730 and 740 will cause the outer sleeve 704, 708 to start gradually retracting towards the handle 701. As a result of this retraction of the outer sleeve, the outer member 780 will gradually disengage the annular portion V1 of the valve V. The annular portion V1 will thus be allowed to radially expand.

Gradual withdrawal of the outer sleeve 704, 708 proceeds until the outer member 780 has almost completely disengaged the valve V, while the annular formation V2 is still securely retained by the intermediate member 770 of the inner sleeve 705, 707 which maintains the annular formation V2 of the valve on the holder portion 709. This deployment mechanism of the annular formation V1 and the valve V may be controlled very precisely by the practitioner via the screw-like mechanism 730, 740 actuated by the rotary member 703. Deployment may take place in a gradual and easily controllable manner by enabling the practitioner to verify how deployment takes place.

In some embodiments, so long as the annular formation V2 of the valve V is still constrained within the formation 709 by the intermediate member 770, the practitioner still retains firm control of the partial (e.g., "basket-like") expanded valve V. The practitioner will thus be able to adjust the position of the valve V both axially and radially (e.g., by rotating the valve V around its longitudinal axis). This radial adjustment allows the practitioner to ensure that radially expanding anchoring formations of the valve V are properly aligned with the Valsalva sinuses to firmly and reliably retain in place the valve V once finally delivered.

With the valve V retained by the device 700 almost exclusively via the intermediate member 770 acting on the annular formation V2, the blocking member 702 can be removed from the shaft 706, thus permitting the inner sleeve 705, 707 (and, if not already effected previously, the outer sleeve 704, 708) to be retracted in such a way to disengage the annular portion V2 of the valve. This movement allows the annular formation V2 (and the valve V as a whole) to become disengaged from the device 700 and thus becoming completely deployed at the implantation site. This movement can be effected by sliding the inner sleeve (and the outer sleeve) towards the handle 701.

In some embodiments, the valves described herein such as the valve 301 (FIG. 19) or the valve 401 (FIG. 20) may be implanted using the delivery devices 501 (FIGS. 21A-B) or 700 (FIG. 23) in a minimally invasive manner. In some embodiments, the delivery devices may be manipulated remotely using a medical robotic system. Suitable medical robotic systems are described, for example, in U.S. Pat. Nos. 6,493,608; 6,424,885 and 7,453,227, each of which are incorporated herein by reference in their entirety. Illustrative but non-limiting examples of medical robotic systems include those available from Intuitive Surgical, Inc., of Sunnyvale Calif. under the da Vinci tradename.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A transapical method of gaining access to an interior of a patient's heart, the method comprising steps of:
    advancing a first hollow needle into a patient's chest through an intercostal space that is above the apex of the patient's heart;
    advancing a guidewire through the first hollow needle;
    advancing an S-shaped catheter through the first hollow needle and over the guidewire such that the S-shaped catheter has a distal end positioned proximate the apex of the patient's heart and exterior to the patient's pericardial sac;
    advancing a second hollow needle through the S-shaped catheter to a position exterior to the patient's pericardial sac;
    penetrating the pericardial sac with the second hollow needle;
    penetrating the heart wall of the patient's heart;
    advancing a first catheter including a first inflatable balloon on a distal region of the first catheter through the second hollow needle and into the patient's heart; and
    inflating the first inflatable balloon to provide a first seal between the first catheter and the heart wall.

2. The method of claim 1, comprising pulling on the first catheter to lift the apex of the heart to a higher position proximate the intercostal space through which the first hollow needle was advanced.

3. The method of claim 1, comprising partially withdrawing the first catheter to lift the apex of the heart to a higher position proximate the intercostal space through which the first hollow needle was advanced.

4. The method of claim 1, wherein penetrating the heart wall of the patient's heart comprises penetrating the heart wall of the patient's heart with the second hollow needle.

5. The method of claim 1, wherein penetrating the heart wall of the patient's heart comprises:
   advancing a cutting catheter bearing a cutting blade through the second hollow needle; and
   penetrating the heart wall with the cutting blade.

6. The method of claim 1, comprising:
   advancing a second catheter including a second inflatable balloon on a distal region of the second catheter through the S-shaped catheter to outside the heart wall; and
   inflating the second inflatable balloon to provide a second seal between the second catheter and the heart wall.

7. The method of claim 1, comprising advancing a port over the first catheter and into the patient's heart to provide access for delivery of a replacement valve.

8. The method of claim 7, comprising deflating the first inflatable balloon prior to advancing the port over the first catheter.

9. The method of claim 7, comprising providing structure in the port to secure the port to the heart wall.

10. The method of claim 7, comprising providing an inner flange and an outer flange on the port to secure the port to the heart wall.

11. The method of claim 7, wherein the port includes an internal valve that permits deliveries through the internal valve while preventing fluids from leaking through the port.

12. A transapical method of gaining access to an interior of a patient's heart, the method comprising steps of:
   advancing a first hollow needle into a patient's chest through an intercostal space that is above the apex of the patient's heart;
   advancing a guidewire through the first hollow needle;
   advancing an S-shaped catheter through the first hollow needle and over the guidewire such that the S-shaped catheter has a distal end positioned proximate the apex of the patient's heart and exterior to the patient's pericardial sac;
   advancing a second hollow needle through the S-shaped catheter to a position exterior to the patient's pericardial sac;
   penetrating the pericardial sac with the second hollow needle;
   penetrating the heart wall of the patient's heart via the second hollow needle; and
   advancing a port into the patient's heart through the penetration in the heart wall made via the second hollow needle to provide access for delivery of a replacement valve.

13. The method of claim 12, comprising:
   advancing a catheter including an inflatable balloon on a distal region of the catheter through the second hollow needle and into the patient's heart; and
   inflating the inflatable balloon to provide a seal between the catheter and the heart wall.

14. The method of claim 13, wherein advancing a port into the patient's heart comprises:
   deflating the inflatable balloon; and
   advancing the port over the catheter including the inflatable balloon.

15. The method of claim 12, comprising providing structure in the port to secure the port to the heart wall.

16. The method of claim 12, comprising providing an inner flange and an outer flange on the port to secure the port to the heart wall.

17. The method of claim 12, wherein the port includes an internal valve that permits deliveries through the internal valve and prevents fluids from leaking through the port.

* * * * *